United States Patent
Patek

(10) Patent No.: US 11,804,289 B2
(45) Date of Patent: Oct. 31, 2023

(54) THERAPEUTIC ZONE ASSESSOR

(71) Applicant: DexCom, Inc., San Diego, CA (US)

(72) Inventor: Stephen D. Patek, Charlottesville, VA (US)

(73) Assignee: DEXCOM, INC., San Diego, CA (US)

( * ) Notice: Subject to any disclaimer, the term of this patent is extended or adjusted under 35 U.S.C. 154(b) by 349 days.

(21) Appl. No.: 17/123,598

(22) Filed: Dec. 16, 2020

(65) Prior Publication Data

US 2021/0193287 A1 Jun. 24, 2021

Related U.S. Application Data

(60) Provisional application No. 62/950,029, filed on Dec. 18, 2019.

(51) Int. Cl.
| | |
|---|---|
| *G16H 20/17* | (2018.01) |
| *G16H 40/67* | (2018.01) |
| *A61B 5/00* | (2006.01) |
| *G16H 10/60* | (2018.01) |
| *A61B 5/145* | (2006.01) |

(Continued)

(52) U.S. Cl.
CPC ........ *G16H 20/17* (2018.01); *A61B 5/14532* (2013.01); *A61B 5/7275* (2013.01); *G06F 16/26* (2019.01); *G06F 40/40* (2020.01); *G16H 10/60* (2018.01); *G16H 15/00* (2018.01); *G16H 20/10* (2018.01); *G16H 20/60* (2018.01); *G16H 40/67* (2018.01); *G16H 50/20* (2018.01); *G16H 50/30* (2018.01); *G16H 50/70* (2018.01);

(Continued)

(58) Field of Classification Search
CPC ........ G16H 20/17; G16H 40/67; G16H 10/60; G16H 15/00; G16H 50/30; G16H 50/70; G16H 50/20; G16H 70/40; G16H 20/10; G16H 20/60; G06F 16/26; G06F 40/40; A61B 5/14532; A61B 5/7275; A61M 5/1723; A61M 2230/201

USPC ........................................ 705/2–3

See application file for complete search history.

(56) References Cited

U.S. PATENT DOCUMENTS

| | | | | |
|---|---|---|---|---|
| 10,102,344 | B2 * | 10/2018 | Rees ............... | A61B 5/4833 |
| 2006/0094947 | A1 * | 5/2006 | Kovatchev ....... | G16H 50/50 |
| | | | | 600/365 |

(Continued)

OTHER PUBLICATIONS

International Search Report and Written Opinion dated Apr. 22, 2021 for Application No. PCT/US2020/65321, filed Dec. 16, 2020; 11 pages.

*Primary Examiner* — Michael Tomaszewski
(74) *Attorney, Agent, or Firm* — Stuart H. Mayer; Kaplan Breyer Schwarz LLP

(57) ABSTRACT

Systems and methods are provided for identifying therapeutic zones where there is glycemic dysfunction of a specific type that can be addressed by making strategic changes to behavior and/or therapy parameters. Systems and methods described herein evaluate large historical data sets to: identify a therapeutic zone or zones with glycemic dysfunction that are most readily addressable; quantify the glycemic impact of a plurality of different therapeutic adjustments in terms of either adjustments to historical doses or the parameters of a prospective dosing strategy to determine the highest possible improvement; and/or identify patient dosing strategies to provide therapy recommendations adapted for the patient's preferred behavioral dosing strategy.

45 Claims, 26 Drawing Sheets

(51) Int. Cl.
*G16H 50/30* (2018.01)
*G16H 70/40* (2018.01)
*G16H 20/10* (2018.01)
*G16H 20/60* (2018.01)
*G06F 40/40* (2020.01)
*G16H 15/00* (2018.01)
*G16H 50/70* (2018.01)
*G16H 50/20* (2018.01)
*G06F 16/26* (2019.01)
*A61M 5/172* (2006.01)

(52) U.S. Cl.
CPC ........... *G16H 70/40* (2018.01); *A61M 5/1723* (2013.01); *A61M 2230/201* (2013.01)

(56) References Cited

U.S. PATENT DOCUMENTS

| | | | | |
|---|---|---|---|---|
| 2008/0154513 | A1* | 6/2008 | Kovatchev | G16H 15/00 702/19 |
| 2011/0319322 | A1* | 12/2011 | Bashan | A61B 5/4839 514/5.9 |
| 2016/0073952 | A1* | 3/2016 | Bashan | G16H 20/17 705/2 |
| 2016/0328991 | A1* | 11/2016 | Simpson | A61B 5/486 |
| 2021/0193279 | A1 | 6/2021 | Patek | |
| 2021/0193287 | A1* | 6/2021 | Patek | G16H 10/60 |
| 2021/0193328 | A1* | 6/2021 | Patek | A61B 5/7275 |

* cited by examiner

900

950

THERAPEUTIC ZONE ASSESSOR

CROSS-REFERENCE TO RELATED APPLICATIONS

This application claims the benefit of priority to U.S. Provisional Patent Application No. 62/950,029, filed on Dec. 18, 2019, entitled "THERAPEUTIC ZONE ASSESSOR," the contents of which are hereby incorporated by reference in its entirety, and is hereby expressly made a part of this specification.

BACKGROUND

With the growing adoption of CGM (continuous glucose monitoring) and connected devices, the availability and reliability of glucose time-series data has increased in recent years.

Identifying multiple patterns in large historic data sets requires a level of complexity that cannot be addressed by human evaluation due at least in part to overlapping symptoms in those patterns. Even with pattern analysis tools, doctors cannot reliably determine what aspect of diabetes therapy is most readily addressable for each unique patient situation based on a review of the data.

Because of the numerous variables and factors involved in diabetes management, current practices for identifying patterns and making recommendations lack a reliability and ease of use that considers things such as credibility of data, therapeutic addressability of certain aspects of diabetes risks, impact improvements, patient-preferred diabetes management strategies, and synthesis of related risks and therapies, for example.

Often times, clinicians review CGM traces for a patient over a period of time, such as 14 days, and corresponding insulin delivery patterns, or review the data in a more consolidated format such as a plot that shows each of the 14 days of data overlaid on a 24 hour timeline in an attempt to visually highlight areas of stronger patterns within a particular time of day.

However, visualization of the data cannot easily highlight many of the important factors, risks, and potential outcomes needed for effective therapy optimization. Additionally, the credibility of the data is unknown or unclear from visual inspection.

It is with respect to these and other considerations that the various aspects and embodiments of the present disclosure are presented.

SUMMARY

Systems and methods are provided for identifying therapeutic zones where there is glycemic dysfunction of a specific type that can be addressed by making strategic changes to behavior and/or therapy parameters.

Systems and methods described herein evaluate large historical data sets to: identify a therapeutic zone or zones with glycemic dysfunction that are most readily addressable; quantify the glycemic impact of a plurality of different therapeutic adjustments in terms of either adjustments to historical doses or the parameters of a prospective dosing strategy to determine the highest possible improvement; and/or identify patient dosing strategies to provide therapy recommendations adapted for the patient's preferred behavioral dosing strategy.

In an implementation, a method comprises: deriving at least one single symptom-specific risk profile, using a glycemic risk profiler; determining, using a therapeutic zone assessor, at least one therapeutically correlated zone associated with the at least one single symptom-specific risk profile; determining, using a zone importance quantifier, an importance value of the at least one therapeutically correlated zone; and outputting information based on the importance value.

Implementations may include some or all of the following features. The method further comprises receiving glucose data, wherein deriving the at least one single symptom-specific risk profile uses the glucose data. The glucose data comprises at least one of CGM (continuous glucose monitoring) readings, confidence readings assigned to CGM values, self-monitoring blood glucose readings, or retrospectively calibrated or corrected CGM readings. The glucose data encompasses a time period of at least one week. The at least one single symptom-specific risk profile describes either hypoglycemic risk or hyperglycemic risk as a function of the time of day using glucose data. Deriving the at least one single symptom-specific risk profile comprises at least one of evaluating steepness (first and second order derivatives of a curve), frequency, severity, curvature, average value of profile across 24 hours, or variability of the profile (mean and standard deviation). The at least one single symptom-specific risk profile is indicative of glycemic dysfunction based the CGM signal over a selected time period, indicating recurring windows of time characterized by a predefined severity and frequency of hypoglycemia or hyperglycemia over the selected time period. The at least one single symptom-specific risk profile represents at least one of hypoglycemia isolated from hyperglycemia, or hyperglycemia isolated from hypoglycemia. Determining the at least one therapeutically correlated zone comprises identifying the at least one therapeutically correlated zone from the at least one single symptom-specific risk profile. The at least one therapeutically correlated zone is an interval of a 24 hour day in which BG data of a patient indicates that at least one of the insulin basal rate or dose or bolus strategies of the patient are systematically non-optimal. The at least one therapeutically correlated zone is identified and associated with at least one risk profile and comprises at least one interval of the day in which one or more single symptom-specific risk profiles indicate potential glycemic dysfunction.

Implementations may also include some or all of the following features. The method further comprises identifying a period of time in which the at least one single symptom-specific risk profile could be mitigated via the adjustment of parameters or timing of insulin therapy. Determining the at least one therapeutically correlated zone is based on which of least one of candidate behavioral changes or therapeutic changes are predicted to decrease a single-symptom glycemic risk without a subsequent increase in another symptom. Determining the importance value of the at least one therapeutically correlated zone comprises prioritizing the zone that is more therapeutically significant or addressable. Determining the importance value of the at least one therapeutically correlated zone comprises evaluating a magnitude of a risk. Determining the importance value of the at least one therapeutically correlated zone comprises considering at least one of the time of day or proximity of one risk profile to another risk profile. The importance value is the peak value of the at least one single symptom-specific risk profile. Deriving the at least one single symptom-specific risk profile is based on data above a particular credibility level. Outputting the information comprises outputting at least one of numerical, alphanumerical, or graphical information. Outputting the information comprises outputting at least one of behavioral changes or therapeutic changes to a therapeutic zone of time to decrease a single symptom in a time window. Outputting the information comprises outputting the information to a connected insulin pump or insulin pen, or into a bolus calculator. Outputting the information comprises outputting a graphical representation of at least one of risk profiles or therapeutically correlated zones, or relative importance of at least one of risk profiles or therapeutically correlated zones.

In an implementation, a system comprises: a glycemic risk profiler configured to derive at least one single symptom-specific risk profile; a therapeutic zone assessor configured to determine at least one therapeutically correlated zone associated with the at least one single symptom-specific risk profile; a zone importance quantifier configured to determine an importance value of the at least one therapeutically correlated zone; and a therapeutic zone report generator configured to output information based on the importance value.

Implementations may include some or all of the following features. The glycemic risk profiler is further configured to receive glucose data, wherein deriving the at least one single symptom-specific risk profile uses the glucose data. The glucose data comprises at least one of CGM (continuous glucose monitoring) readings, confidence readings assigned to CGM values, self-monitoring blood glucose readings, or retrospectively calibrated or corrected CGM readings. The glucose data encompasses a time period of at least one week. The at least one single symptom-specific risk profile describes either hypoglycemic risk or hyperglycemic risk as a function of the time of day using glucose data. Deriving the at least one single symptom-specific risk profile comprises at least one of evaluating steepness (first and second order derivatives of a curve), frequency, severity, curvature, average value of profile across 24 hours, or variability of the profile (mean and standard deviation). The at least one single symptom-specific risk profile is indicative of glycemic dysfunction based the CGM signal over a selected time period, indicating recurring windows of time characterized by a predefined severity and frequency of hypoglycemia or hyperglycemia over the selected time period. The at least one single symptom-specific risk profile represents at least one of hypoglycemia isolated from hyperglycemia, or hyperglycemia isolated from hypoglycemia. Determining the at least one therapeutically correlated zone comprises identifying the at least one therapeutically correlated zone from the at least one single symptom-specific risk profile. The at least one therapeutically correlated zone is an interval of a 24 hour day in which BG data of a patient indicates that at least one of the insulin basal rate or dose or bolus strategies of the patient are systematically non-optimal. The at least one therapeutically correlated zone is identified and associated with at least one risk profile and comprises at least one interval of the day in which one or more single symptom-specific risk profiles indicate potential glycemic dysfunction.

Implementations may also include some or all of the following features. The therapeutic zone assessor is further configured to identify a period of time in which the at least one single symptom-specific risk profile could be mitigated via the adjustment of parameters or timing of insulin therapy. Determining the at least one therapeutically correlated zone is based on which of least one of candidate behavioral changes or therapeutic changes are predicted to decrease a single-symptom glycemic risk without a subsequent increase in another symptom. Determining the importance value of the at least one therapeutically correlated zone comprises prioritizing the zone that is more therapeutically significant or addressable. Determining the importance value of the at least one therapeutically correlated zone comprises evaluating a magnitude of a risk. Determining the importance value of the at least one therapeutically correlated zone comprises considering at least one of the time of day or proximity of one risk profile to another risk profile. The importance value is the peak value of the at least one single symptom-specific risk profile. Deriving the at least one single symptom-specific risk profile is based on data above a particular credibility level. Outputting the information comprises outputting at least one of numerical, alpha-numerical, or graphical information. Outputting the information comprises outputting at least one of behavioral changes or therapeutic changes to a therapeutic zone of time to decrease a single symptom in a time window. Outputting the information comprises outputting the information to a connected insulin pump or insulin pen, or into a bolus calculator. Outputting the information comprises outputting a graphical representation of at least one of risk profiles or therapeutically correlated zones, or relative importance of at least one of risk profiles or therapeutically correlated zones.

In an implementation, a system comprises: at least one processor; and a non-transitory computer readable medium comprising instructions that, when executed by the at least one processor, cause the system to: derive at least one single symptom-specific risk profile; determine at least one therapeutically correlated zone associated with the at least one single symptom-specific risk profile; determine an importance value of the at least one therapeutically correlated zone; and output information based on the importance value.

Implementations may include some or all of the following features. The system further comprises instructions that, when executed by the at least one processor, cause the system to receive glucose data, wherein deriving the at least one single symptom-specific risk profile uses the glucose data. The glucose data comprises at least one of CGM (continuous glucose monitoring) readings, confidence readings assigned to CGM values, self-monitoring blood glucose readings, or retrospectively calibrated or corrected CGM readings. The glucose data encompasses a time period of at least one week. The at least one single symptom-specific risk profile describes either hypoglycemic risk or hyperglycemic risk as a function of the time of day using glucose data. Deriving the at least one single symptom-specific risk profile comprises at least one of evaluating steepness (first and second order derivatives of a curve), frequency, severity, curvature, average value of profile across 24 hours, or variability of the profile (mean and standard deviation). The at least one single symptom-specific risk profile is indicative of glycemic dysfunction based the CGM signal over a selected time period, indicating recurring windows of time characterized by a predefined severity and frequency of hypoglycemia or hyperglycemia over the selected time period. The at least one single symptom-specific risk profile represents at least one of hypoglycemia isolated from hyperglycemia, or hyperglycemia isolated from hypoglycemia. Determining the at least one therapeutically correlated zone comprises identifying the at least one therapeutically correlated zone from the at least one single symptom-specific risk profile. The at least one therapeutically correlated zone is an interval of a 24 hour day in which BG data of a patient indicates that at least one of the insulin basal rate or dose or bolus strategies of the patient are systematically non-optimal. The at least one therapeutically correlated zone is identified and associated with at least one risk profile and comprises at least one interval of the day in which one or more single symptom-specific risk profiles indicate potential glycemic dysfunction.

Implementations may also include some or all of the following features. The system further comprises instructions that, when executed by the at least one processor, cause the system to identify a period of time in which the at least one single symptom-specific risk profile could be mitigated via the adjustment of parameters or timing of insulin therapy. Determining the at least one therapeutically correlated zone is based on which of least one of candidate behavioral changes or therapeutic changes are predicted to decrease a single-symptom glycemic risk without a subsequent increase in another symptom. Determining the importance value of the at least one therapeutically correlated zone comprises prioritizing the zone that is more therapeutically significant or addressable. Determining the importance value of the at least one therapeutically correlated zone comprises evaluating a magnitude of a risk. Determining the importance value of the at least one therapeutically correlated zone comprises considering at least one of the time of day or proximity of one risk profile to another risk profile. The importance value is the peak value of the at least one single symptom-specific risk profile. Deriving the at least one single symptom-specific risk profile is based on data above a particular credibility level. Outputting the information comprises outputting at least one of numerical, alphanumerical, or graphical information. Outputting the information comprises outputting at least one of behavioral changes or therapeutic changes to a therapeutic zone of time to decrease a single symptom in a time window. Outputting the information comprises outputting the information to a connected insulin pump or insulin pen, or into a bolus calculator. Outputting the information comprises outputting a graphical representation of at least one of risk profiles or therapeutically correlated zones, or relative importance of at least one of risk profiles or therapeutically correlated zones.

In an implementation, a method comprises: receiving glucose and insulin data; identifying a therapeutic improvement opportunity using the glucose and insulin data; determining candidate changes to insulin therapy; assessing an improvement in therapeutic risk based on the candidate changes; quantifying the improvement of the candidate changes; and outputting at least one of the candidate changes based on the improvement.

Implementations may include some or all of the following features. The glucose and insulin data is received from at least one of a patient or a connected system or device. Identifying the therapeutic improvement opportunity comprises receiving a user selection of at least one of a mealtime, a time of day, or a parameter setting. The parameter setting is a carb ratio. The candidate changes to insulin therapy comprise percentage increases or decreases to bolus therapy or basal therapy. The candidate changes to insulin therapy comprise changes to insulin delivery parameters associated with bolus therapy or basal therapy. The candidate changes are in terms of carb ratios, correction factors, basal rates, or profiles. The candidate changes comprise basal dose sensitivity. The candidate changes comprise percentage change to basal or bolus doses in therapeutic zones. Quantifying the improvement of the candidate changes comprises comparing risk profile values. Outputting at least one of the candidate changes based on the improvement comprises outputting the candidate change that provides the optimized risk profile. Outputting at least one of the candidate changes comprises providing an output in the form of a graph illustrating at least one of a candidate change or an optimized risk output to a user interface or connected device. The connected device comprises a bolus calculator. The output is provided by a natural language processor to describe a candidate change and an optimized risk outcome. The output identifies which therapeutic zones or zone groups have been optimized.

In an implementation, a system comprises: a therapeutic improvement identifier configured to evaluate collated glucose and insulin data of a patient to identify areas for therapy optimization in a diabetes management routine of the patient, and to generate a therapeutic improvement; a relative insulin optimizer configured to propose changes to a therapy, assess the impact of the changes, and quantifies an improvement associated with the changes; and a relative insulin optimizer report generator that provides an output.

Implementations may include some or all of the following features. The relative insulin optimizer comprises: a change proposer configured to propose the changes to insulin therapy; an impact assessor configured to assess the impact of candidate therapy changes by estimating the impact to a risk profile of historical glucose values; and an improvement quantifier configured to quantify an improvement of candidate therapy changes. The change proposer is further configured to propose the changes as percentage-wise changes to at least one of basal or bolus in a time window. The improvement quantifier is configured to quantify the improvement of candidate therapy changes, based on a percentage improvement or change in blood glucose outcome metrics. The relative insulin optimizer report generator is configured to output candidate therapy change to a user. The user is one of a clinician, a patient, or a connected device or system. The therapeutic improvement identifier comprises a user selection of a therapy or a time of day to be optimized. The user is a patient or a clinician. The therapeutic improvement is identified by an algorithm.

In an implementation, a system comprises: at least one processor; and a non-transitory computer readable medium comprising instructions that, when executed by the at least one processor, cause the system to: receive glucose and insulin data; identify a therapeutic improvement opportunity using the glucose and insulin data; determine candidate changes to insulin therapy; assess an improvement in therapeutic risk based on the candidate changes; quantify the improvement of the candidate changes; and output at least one of the candidate changes based on the improvement.

Implementations may include some or all of the following features. The glucose and insulin data is received from at least one of a patient or a connected system or device. Identifying the therapeutic improvement opportunity comprises receiving a user selection of at least one of a mealtime, a time of day, or a parameter setting. The parameter setting is a carb ratio. The candidate changes to insulin therapy comprise percentage increases or decreases to bolus therapy or basal therapy. The candidate changes to insulin therapy comprise changes to insulin delivery parameters associated with bolus therapy or basal therapy. The candidate changes are in terms of carb ratios, correction factors, basal rates, or profiles. The candidate changes comprise basal dose sensitivity. The candidate changes comprise percentage change to basal or bolus doses in therapeutic zones. Quantifying the improvement of the candidate changes comprises comparing risk profile values. Outputting at least one of the candidate changes based on the improvement comprises outputting the candidate change that provides the optimized risk profile. Outputting at least one of the candidate changes comprises providing an output in the form of a graph illustrating at least one of a candidate change or an optimized risk output to a user interface or connected device. The connected device comprises a bolus calculator. The output is provided by a natural language processor to describe a candidate change and an optimized risk outcome. The output identifies which therapeutic zones or zone groups have been optimized.

In an implementation, a method comprises: receiving at least one of glucose data, insulin data, or other-diabetes related data of a patient; identifying a therapeutic improvement opportunity using the at least one of glucose data, insulin data, or other-diabetes related data; identifying an insulin dosing strategy of the patient; scoring the insulin dosing strategy for patient compliance; performing optimization for the insulin dosing strategy; and providing an output comprising optimized insulin strategy parameters to a user.

Implementations may include some or all of the following features. The other diabetes-related data comprises at least one of meal information, specificity of meals, timing of meals, sizing of meals, carbohydrate estimates, composition information, or exercise information. The at least one of glucose data, insulin data, or other-diabetes related data is received from at least one of a patient or a connected system or device. Identifying the therapeutic improvement opportunity comprises receiving a user selection of at least one of a mealtime, a time of day, or a parameter setting. The parameter setting is a carb ratio. The insulin dosing strategy comprises a diabetes management or insulin strategy being implemented by the patient in practice as determined from the at least one of glucose data, insulin data, or other-diabetes related data of a patient. Performing optimization for the insulin dosing strategy determines whether the patient adheres to a known insulin strategy and analyzes the effect of percentage changes to the parameters of the identified insulin strategy. The user is at least one of a clinician, a patient, or a connected device or system. The output is provided by a natural language processor to describe a candidate change and an optimized risk outcome. Providing the output comprises providing an output in the form of a graph illustrating the optimized insulin strategy parameters to a user interface or connected device. The connected device comprises a bolus calculator.

In an implementation, a system comprises: a therapeutic improvement identifier configured to evaluate collated glucose and insulin data of a patient to identify areas for therapy optimization in a diabetes management routine of the patient, and to generate a therapeutic improvement; an insulin strategy optimizer configured to determine whether the patient adheres to a known insulin strategy and analyze the effect of percentage changes to the parameters of the identified insulin strategy; and a therapy identifier optimizer report generator that provides an output.

Implementations may include some or all of the following features. The insulin strategy optimizer comprises: an insulin strategy identifier configured to identify a diabetes management or insulin strategy being implemented by the patient in practice as determined from the collated glucose and insulin data; a compliance scorer configured to quantify a compliance of the patient with the identified insulin strategy; and an insulin strategy optimizer within identified behavior configured to perform optimization for the identified insulin strategy. The diabetes data comprises insulin data and meal data. The insulin strategy identifier is configured to identify patterns in dosing and characterizes the identified insulin strategy of the patient based thereon. The insulin strategy is the behavioral methodology that the patient applies in diabetes management, comprising at least one of types of insulin pump usage, multiple daily injections, or type 2 therapies. The compliance scorer is configured to generate a score computed for a degree of compliance of the patient with the identified insulin strategy. The insulin strategy optimizer within identified behavior is configured to iteratively propose percentage changes to the parameters of the strategy in a selected therapeutic zone or zone group. The output comprises optimized insulin strategy parameters. The therapy identifier optimizer report generator is configured to output a candidate therapy change to a user. The user is at least one of a clinician, a patient, or a connected device or system. The output is provided by a natural language processor to describe a candidate change and an optimized risk outcome.

In an implementation, a system comprises: at least one processor; and a non-transitory computer readable medium comprising instructions that, when executed by the at least one processor, cause the system to: receive at least one of glucose data, insulin data, or other-diabetes related data of a patient; identify a therapeutic improvement opportunity using the at least one of glucose data, insulin data, or other-diabetes related data; identify an insulin dosing strategy of the patient; score the insulin dosing strategy for patient compliance; perform optimization for the insulin dosing strategy; and provide an output comprising optimized insulin strategy parameters to a user.

Implementations may include some or all of the following features. The other diabetes-related data comprises at least one of meal information, specificity of meals, timing of meals, sizing of meals, carbohydrate estimates, composition information, or exercise information. The at least one of glucose data, insulin data, or other-diabetes related data is received from at least one of a patient or a connected system or device. Identifying the therapeutic improvement opportunity comprises receiving a user selection of at least one of a mealtime, a time of day, or a parameter setting. The parameter setting is a carb ratio. The insulin dosing strategy comprises a diabetes management or insulin strategy being implemented by the patient in practice as determined from the at least one of glucose data, insulin data, or other-diabetes related data of a patient. Performing optimization for the insulin dosing strategy determines whether the patient adheres to a known insulin strategy and analyzes the effect of percentage changes to the parameters of the identified insulin strategy. The user is at least one of a clinician, a patient, or a connected device or system. The output is provided by a natural language processor to describe a candidate change and an optimized risk outcome. Providing the output comprises providing an output in the form of a graph illustrating the optimized insulin strategy parameters to a user interface or connected device. The connected device comprises a bolus calculator.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

Figure 1:
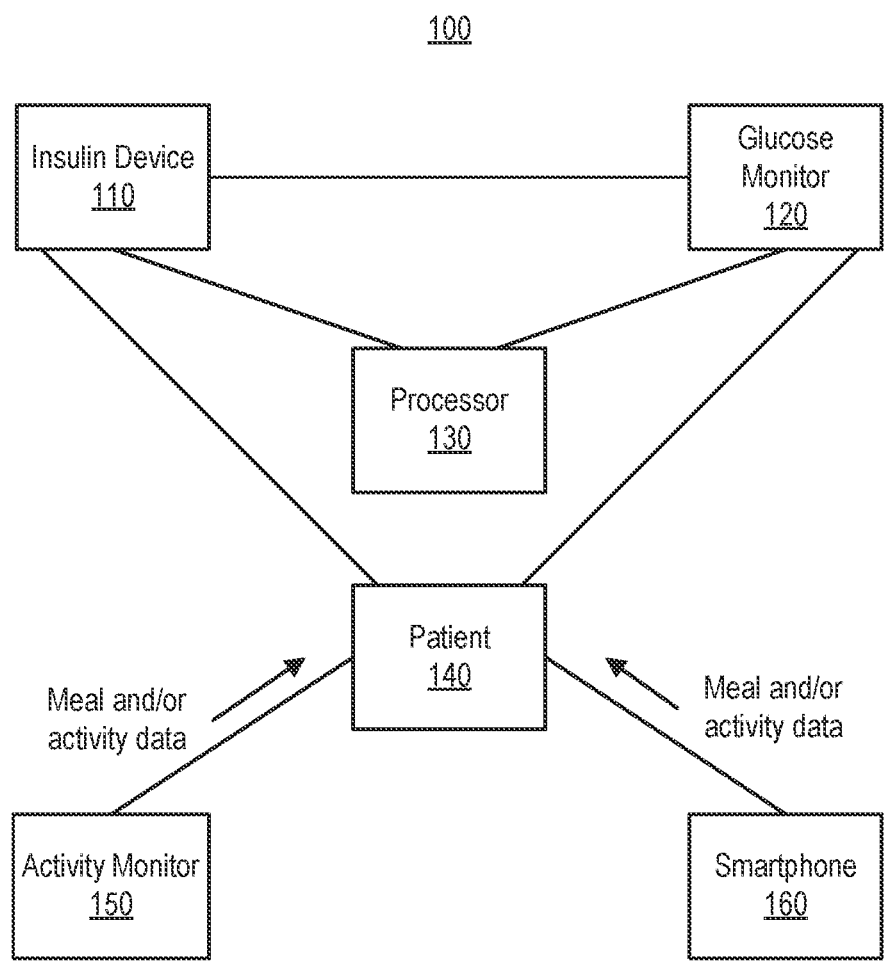
FIG. 1 is a high level functional block diagram of an embodiment of the invention.

The claimed subject matter is described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

FIG. 1 is a high level functional block diagram 100 of an embodiment of the invention. A processor 130 communicates with an insulin device 110 and a glucose monitor 120. The insulin device 110 and the glucose monitor 120 communicate with a patient 140 to deliver insulin to the patient 140 and monitor glucose levels of the patient 140, respectively. The processor 130 is configured to perform the calculations and other operations and functions described further herein. The insulin device 110 and the glucose monitor 120 may be implemented as separate devices or as a single device, within a single device, or across multiple devices. The processor 130 can be implemented locally in the insulin device 110, the glucose monitor 120, or as a standalone device (or in any combination of two or more of the insulin device 110, the glucose monitor 120, or a standalone device). The processor 130 or a portion of the system can be located remotely such as within a server or a cloud-based system.

Examples of insulin devices, such as the insulin device 110, include insulin syringes, external pumps, and patch pumps that deliver insulin to a patient, typically into the subcutaneous tissue. Insulin devices 110 also includes devices that deliver insulin by different means, such as insulin inhalers, insulin jet injectors, intravenous infusion pumps, and implantable insulin pumps. In some embodiments, a patient will use two or more insulin delivery devices in combination, for example injecting long-acting insulin with a syringe and using inhaled insulin before meals. In other embodiments, these devices can deliver other drugs that help control glucose levels such as glucagon, pramlintide, or glucose-like peptide-1 (GLP-1).

Examples of a glucose monitor, such as the glucose monitor 120, include continuous glucose monitors that record glucose values at regular intervals, e.g., 1, 5, or 10 minutes, etc. These continuous glucose monitors can use, for example, electrochemical or optical sensors that are inserted transcutaneously, wholly implanted, or measure tissue non-invasively. Examples of a glucose monitor, such as the glucose monitor 120, also include devices that draw blood or other fluids periodically to measure glucose, such as intravenous blood glucose monitors, microperfusion sampling, or periodic finger sticks. In some embodiments, the glucose readings are provided in near realtime. In other embodiments, the glucose reading determined by the glucose monitor can be stored on the glucose monitor itself for subsequent retrieval.

Figure 26:
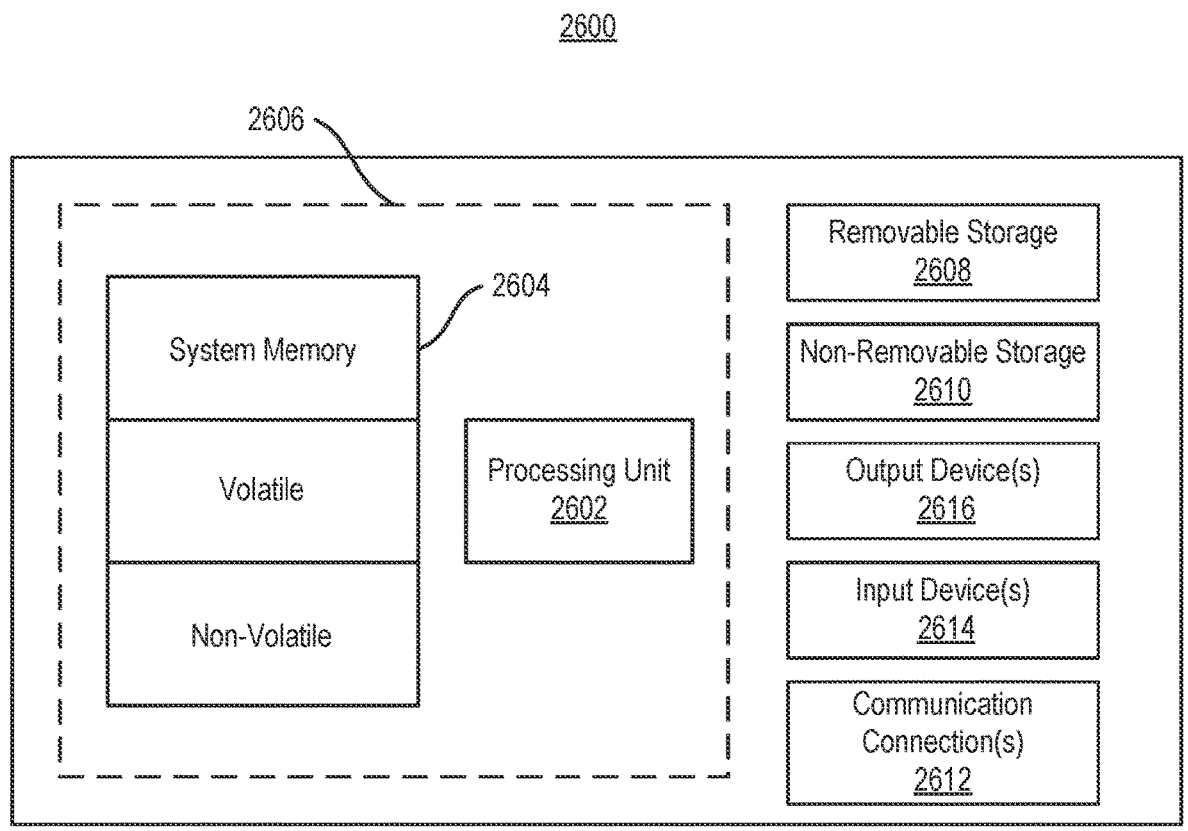
FIG. 26 shows an exemplary computing environment in which example embodiments and aspects may be implemented.

The insulin device 110, the glucose monitor 120, and the processor 130 may be implemented using a variety of computing devices such as smartphones, desktop computers, laptop computers, and tablets. Other types of computing devices may be supported. A suitable computing device is illustrated in FIG. 26 as the computing device 2600 and cloud-based applications.

The insulin device 110, the glucose monitor 120, and the processor 130 may be in communication through a network. The network may be a variety of network types including the public switched telephone network (PSTN), a cellular telephone network, and a packet switched network (e.g., the Internet). Although only one insulin device 110, one glucose monitor 120, and one processor 130 are shown in FIG. 1, there is no limit to the number of insulin devices, glucose monitors, and processors that may be supported. An activity monitor 150 and/or a smartphone 160 may also be used to collect meal and/or activity data from or pertaining to the patient 140, and provide the meal and/or activity data to the processor 130.

The processor 130 may execute an operating system and one or more applications. The operating system may control which applications are executed by the insulin device 110 and/or the glucose monitor 120, as well as control how the applications interact with one or more sensors, services, or other resources of the insulin device 110 and/or the glucose monitor 120.

The processor 130 receives data from the insulin device 110 and the glucose monitor 120, as well as from the patient 140 in some implementations, and may be configured and/or used to perform one or more of the calculations, operations, and/or functions described further herein.

Figure 2:
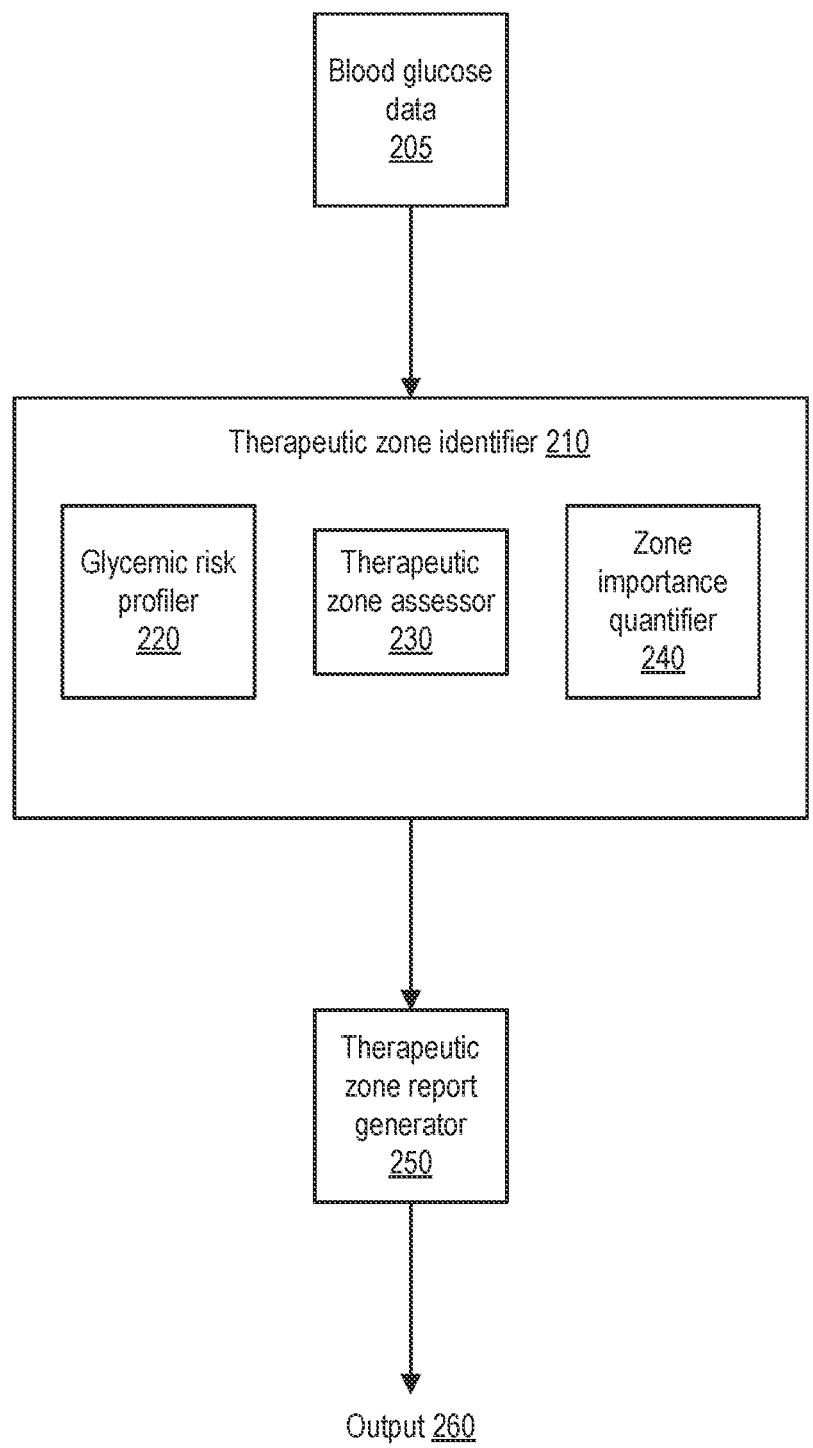
FIG. 2 is a system diagram of an implementation of a therapeutic zone identifier.

FIG. 2 is a system diagram of an implementation of a therapeutic zone identifier 210, which provides a general framework for the therapeutic zone identification system described herein. As shown, the system uses blood glucose data 205, which may be any diabetes data associated with a host, such as a human, and may include CGM only data, BG (blood glucose) data, or other glucose or diabetes-related data, depending on the implementation.

The therapeutic zone identifier 210 identifies an interval of the 24 hour day in which the patient's BG data suggests that the patient's medication dose/strategy needs improvement, e.g., the patient's insulin basal rate/dose and/or bolus strategies are systematically non-optimal or are putting the patient at risk of diabetic complications. In an implementation, the therapeutic zone identifier 210 uses only blood glucose data (e.g., not insulin data), such as data from the glucose monitor 120.

The glycemic risk profiler 220 quantifies the experience of hypoglycemia, hyperglycemia, or both (variable risk) on average across multiple days by quantifying risk as a pattern.

The therapeutic zone assessor 230 evaluates the risk profile and assesses one or more windows of time over which doses could be adjusted for systematic improvement of glycemic outcomes related to one or more correlated features of the risk profile. The time of day is often an important factor to be considered.

The zone importance quantifier 240 quantifies the relative importance of the therapeutic zones.

The report generator 250 provides output 260 in numerical, alphanumerical, and/or graphical information based on the quantified importance of the therapeutically correlated zones.

Figure 3:
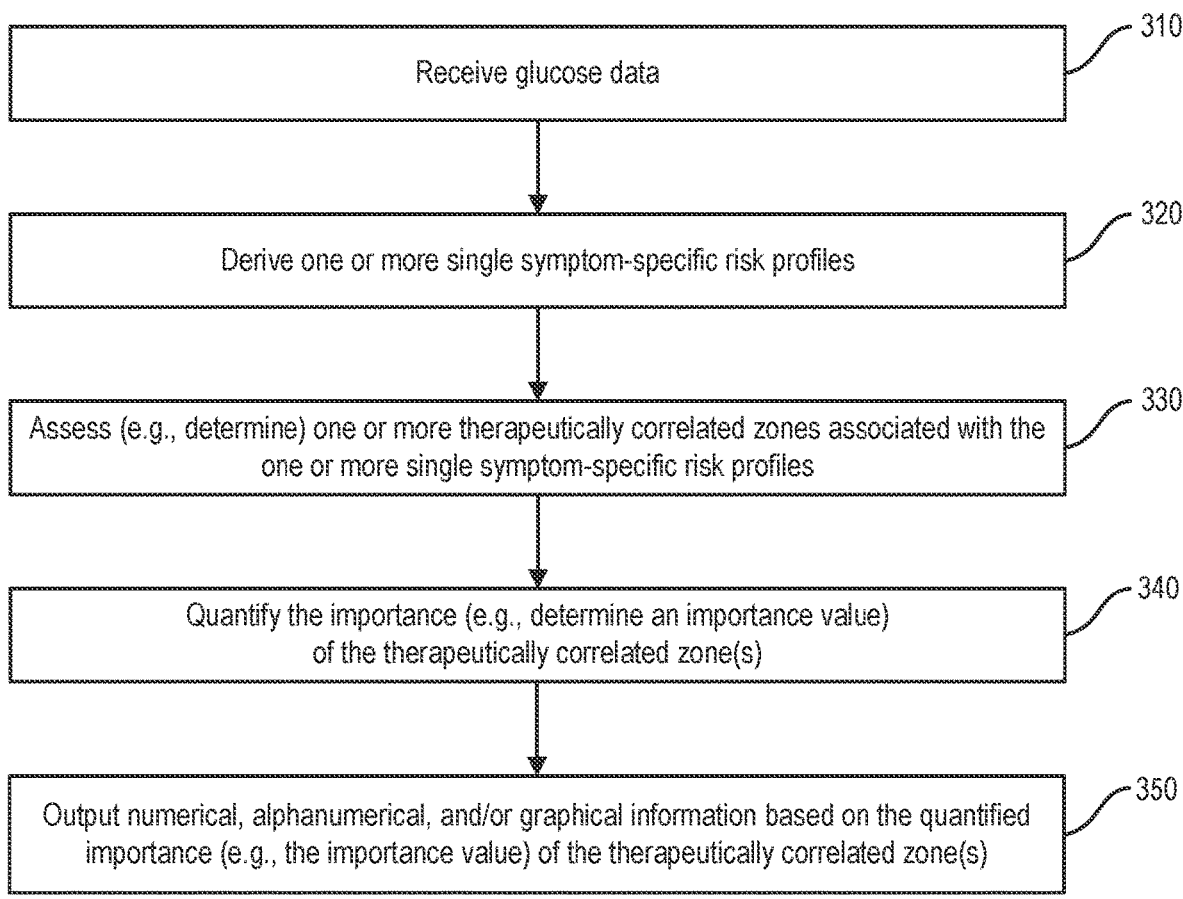
FIG. 3 is a flow diagram for a method of identifying therapeutic zones with potential for improving glycemic outcomes.

FIG. 3 is a flow diagram for a method 300 of identifying therapeutic zones with potential for improving glycemic outcomes. The method 300 of identifying the therapeutic zones with the potential for improving glycemic outcomes includes evaluating large historical data sets to identify a therapeutic zone with glycemic dysfunction that is most readily addressable.

Figure 4:
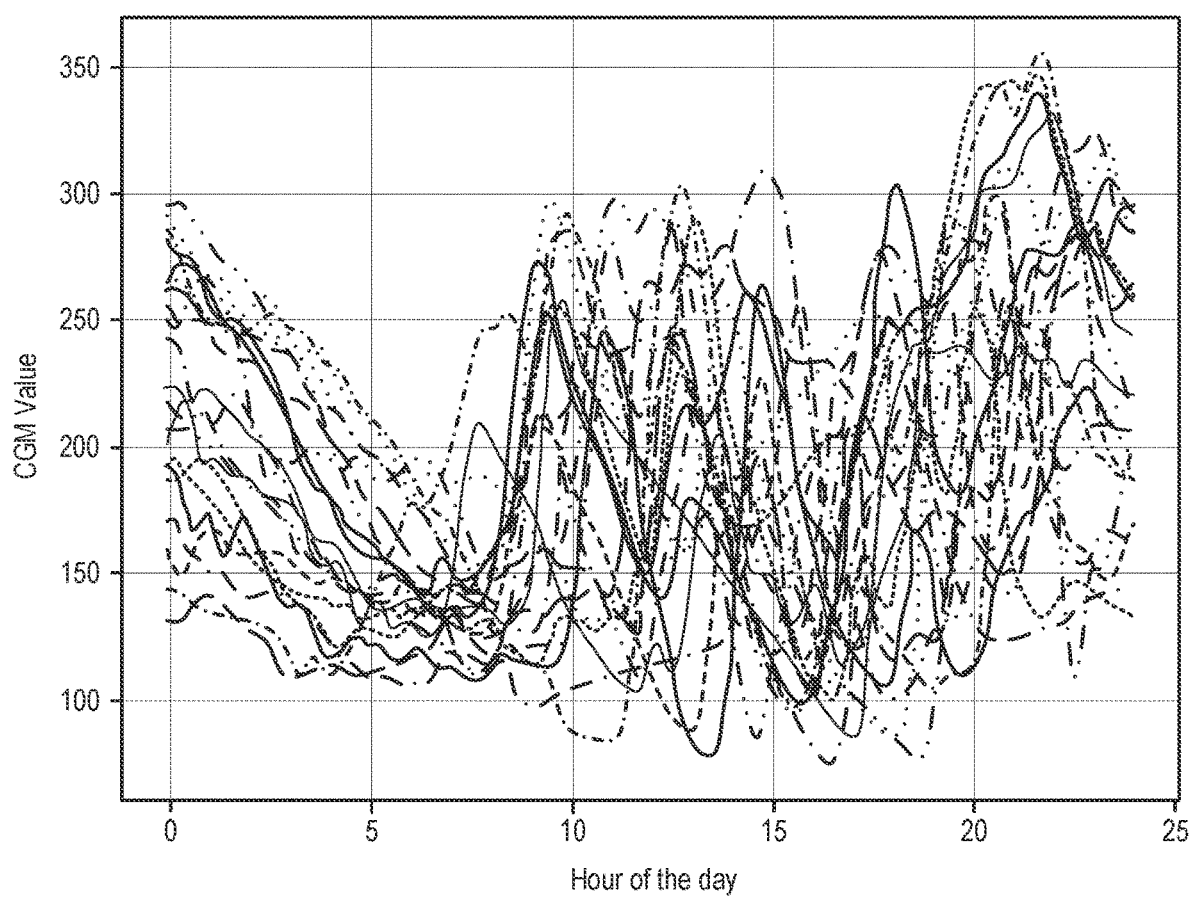
FIG. 4 is a diagram that illustrates one example of CGM data for multiple days overlaid on a 24 hour time window from one patient with type 1 diabetes.

At 310, glucose data is received (e.g., from the glucose monitor 120, the patient 140, the activity monitor 150, and/or the smartphone 160, in some implementations). These data typically comprise measurements of glucose levels including, for example: CGM readings, confidence readings assigned to the CGM values, self-monitoring blood glucose readings (blood glucose meter), retrospectively calibrated or corrected CGM readings, and the like. The glucose data generally encompasses a selected time period of at least one week; however, larger data sets may provide longer-term patterns. The glucose data provides for retrospective analysis of CGM as a function of time of day (e.g., within a 24 hour day). FIG. 4 is a diagram 400 that illustrates one example of CGM data for multiple days overlaid on a 24 hour time window from one patient with type 1 diabetes.

At 320, one or more single symptom-specific risk profiles are derived. More particularly, profiles of single-symptom glycemic dysfunction are assessed, describing either hypoglycemic risk or hyperglycemic risk as a function of the time of day using glucose data received at 310. Risk profiles may be derived using any known glycemic risk quantifier, for example, such as those described in US 2018/0020988 entitled "Method, system and computer readable medium for assessing actionable glycemic risk", inventor Stephen D. Patek, which is incorporated by reference herein in its entirety. A glycemic risk quantifier may evaluate, for example, steepness (first and second order derivatives of a curve), frequency, severity, curvature, average value of profile across 24 hours, variability of the profile (mean and standard deviation), and the like, all of which could be meaningful in terms of identifying the zones. Glycemic risk quantifiers include anything that attaches a score or value to risk, such as low blood glucose index (LBGI) and high blood glucose index (HBGI). The glycemic risk quantifier may quantify the experience of hypoglycemia, hyperglycemia, and/or both in historic data. In some implementations, the method addresses multiple types of risk at the same time of the day or adjacent times of corresponding to the experience of both hyperglycemia and hypoglycemia at the time of day on different days of the historical record.

In some embodiments, the one or more single symptom-specific risk profiles are indicative of glycemic dysfunction based the CGM signal over the selected time period, indicating recurring windows of time (recurring at the same time period within each 24 hour period) characterized by a predefined severity and frequency of a single symptom (e.g., hypoglycemia or hyperglycemia) over the selected time period based on an analysis of the one or more single symptom-specific signals.

In some embodiments, times of the day are identified with a consistent pattern of hypoglycemia, hyperglycemia, and/or both.

In some embodiments, the single symptom-specific risk profiles represent at least one of a) hypoglycemia isolated from hyperglycemia or b) hyperglycemia isolated from hypoglycemia. In an exemplary embodiment, wherein the single symptom is hypoglycemia, the quantifier may evaluate the risk index value below a threshold and duration above a threshold, for example, average glucose less than or equal to 70 mg/dl for 30 minutes. In an exemplary embodiment, wherein the single symptom is hyperglycemia, the quantifier may evaluate the risk index value a above a threshold and duration above a threshold, for example, average glucose greater than or equal to 180 mg/dl for 2 hours.

Other single symptom-specific risk profiles could be defined and evaluated, for example, with A1c greater than a threshold, combinations of health data including diet and exercise as well as cognitive symptoms, which may be measured using techniques known in the art.

Figure 5:
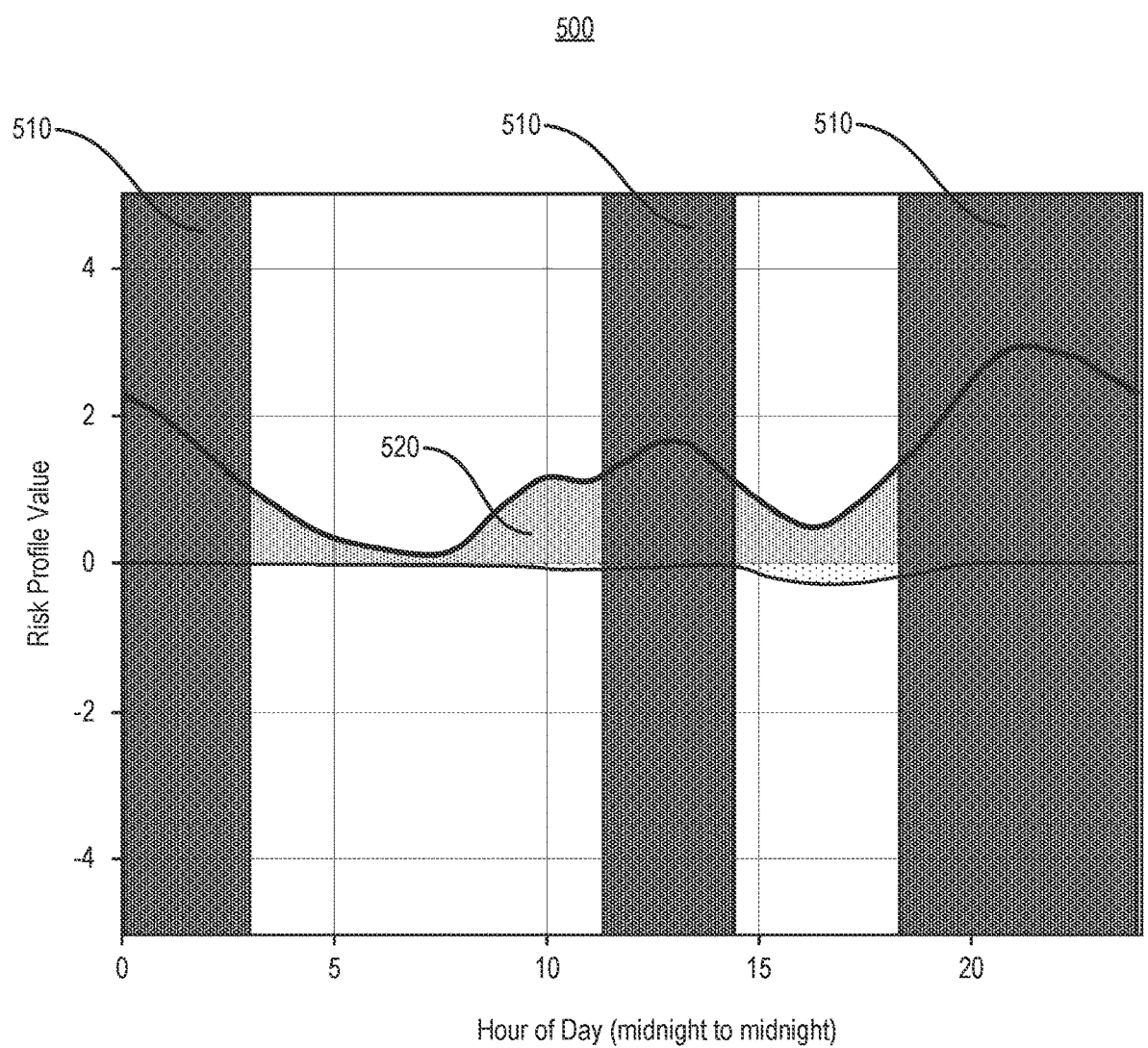
FIG. 5 is a diagram that illustrates one example of single symptom-specific risk profile based on a glycemic risk quantifier.

Preferably, single symptom-specific signals are determined within a single time period within a 24 hour day to avoid mixed glycemic dysfunction. However, other divisions of time, for example weekday vs. weekend, may be evaluated as well. In general, single symptom-specific signals are those wherein, during a specific time period, there is no concurrent single symptom-specific signal of a different type of a predefined severity or frequency. For example, wherein a single hypoglycemia risk profile may not have concurrent hyperglycemia above a value/duration threshold. FIG. 5 is a diagram 500 that illustrates one example of single symptom-specific risk profile 510 based on a risk quantification 520 provided by a glycemic risk quantifier, which was derived from the glucose data of the patient shown at FIG. 4. The risk profile 510 is identified based on the magnitude of the risks shown by the risk quantification 520.

At 330, one or more therapeutically correlated zones associated with the one or more single symptom-specific risk profiles are assessed (e.g., determined). In other words, therapeutic zones are identified from the risk profiles.

In general, within the context of insulin therapy, a therapeutic zone is an interval of the 24 hour day in which the patient's BG data suggests (e.g., indicates) that the patient's insulin basal rate/dose and/or bolus strategies are systematically non-optimal. Other contexts, in relation to other therapies, such as glucagon, type 2 drugs, or even food, may also have therapeutic zones assessed accordingly as may be appreciated by one skilled in the art.

In some embodiments, therapeutic zones are identified and associated with risk profiles which are considered to be intervals of the day in which one or more single symptom-specific risk profiles indicate potential glycemic dysfunction. In some cases, the identified therapeutic zone is associated with the presence of just one symptom, e.g., an isolated period of the day in which there is a risk of hypoglycemia (or conversely a risk of hyperglycemia). In such cases, the therapeutic zone can be identified as a window of time, different from (e.g., expanded around, separate from, adjacent to, and/or overlapping with) the associated glycemic risk profile as the window of time where the root cause behavior/therapy change can be made to mitigate the glycemic, e.g., by systematically reducing insulin in an interval of the day (the therapeutic zone) so as to alleviate the corresponding hypoglycemia risk profile (or conversely by systematically increasing insulin in the therapeutic zone to alleviate a corresponding hyperglycemia risk profile).

In other cases, the therapeutic zone assessor 230 can associate more than one therapeutically correlated single-symptom risk profiles to one or more therapeutic zones. For example, the patient's risk profile may indicate (1) a risk of hyperglycemia in a specific interval of the day (i.e., a hyperglycemia risk profile) with, in another later interval, a period of hypoglycemic risk (i.e., a subsequent correlated hypoglycemia risk profile) or a period of unaddressable risk (i.e., a subsequent correlated interval in which the historical data indicates exposure to both hyperglycemia and hypoglycemia), and the corresponding identified therapeutic zone (or zones) would represent a period (or periods) of the day where the multiple correlated risk profiles could be mitigated via the adjustment of the parameters or timing of insulin therapy (e.g., by more effectively addressing the source of the initial hyperglycemia thereby avoiding the circumstances that can promote hypoglycemia in the later interval of time). In such cases, the associated multiple risk profiles could be immediately adjacent, or could be separated by periods (intervals of the day) expressing no glycemic risk. In this way, adjacent or subsequent zones may be combined, due to their dependence, and addressed via therapeutic adjustments in a single therapeutic zone. For example, when a pattern of hypoglycemia is consistently followed by hyperglycemia, the risk profiles are therapeutically related, perhaps due to overcorrections, and addressed by adjustment to the patient's correction factor to a single therapeutic zone, sometimes referred to as a singleton, in some embodiments. The prior art fails to consider the potential for multiple correlated glycemic risks to be addressed through therapeutic adjustments within one or more comprehensive therapeutic zones. In contrast, the systems and methods described herein extract therapeutic meaning by combining risk with therapeutic zones.

Figure 6:
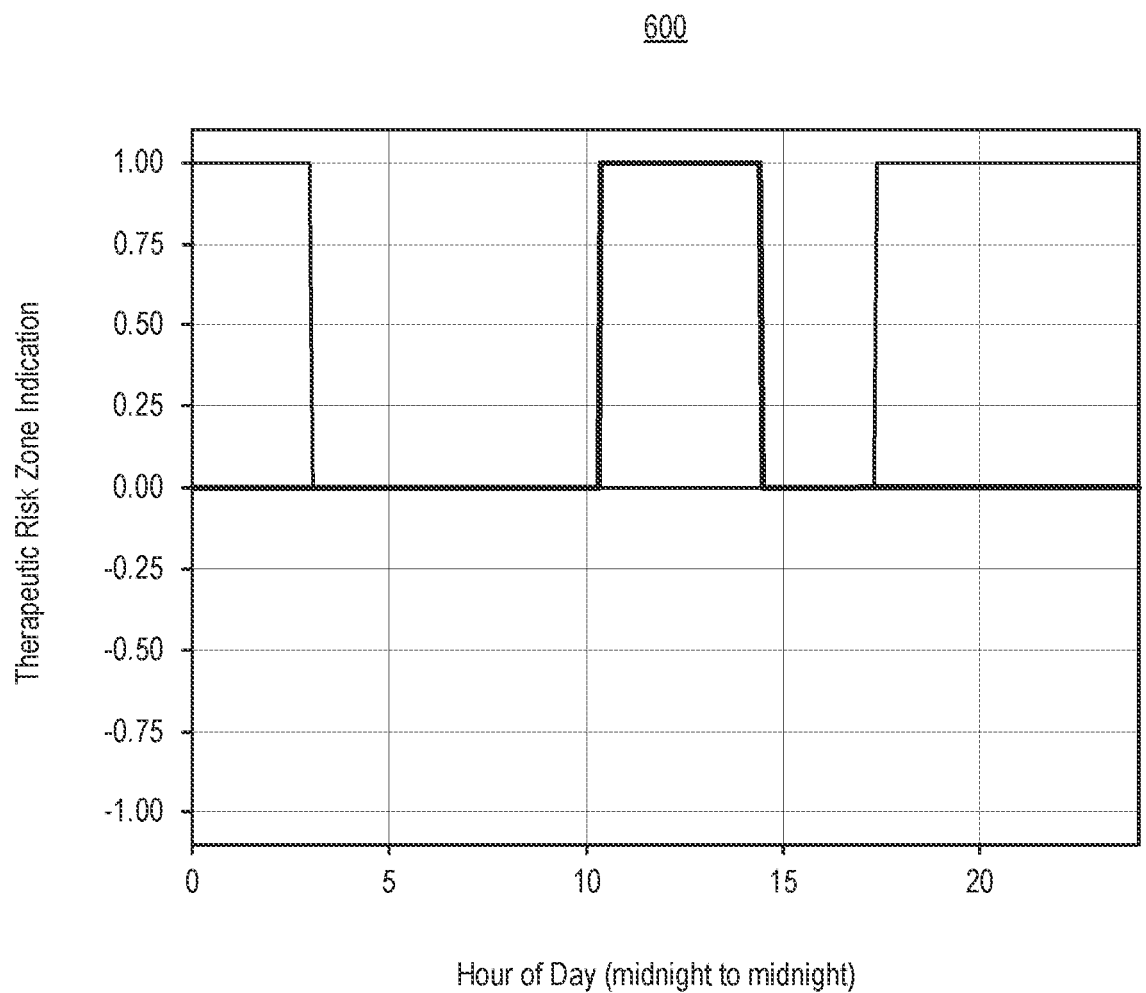
FIG. 6 is a graph that illustrates one example of identified therapeutic zones derived from the single symptom-specific risk profiles.

FIG. 6 is a graph 600 that illustrates one example of identified therapeutic zones derived from the single symptom-specific risk profiles in FIG. 5, which was derived from the glucose data of the patient's CGM data shown in FIG. 4.

In some embodiments, assessment of a risk profile to determine a therapeutic zone is more than just a threshold, for example, could be steepness (first and second order derivatives of a curve), frequency, severity, curvature, average value of profile across 24 hours, variability of the profile (mean and standard deviation) and the like, all of which could be meaningful in terms of identifying the zones.

In some embodiments, the therapeutic zones are assessed based on which candidate behavioral and/or therapeutic changes are predicted to decrease the single-symptom glycemic risk without a subsequent increase in another symptom. In other words, a therapeutic zone may be considered a zone that may be therapeutically addressed without risk to negatively affecting symptoms in adjacent time windows. In some cases, the therapeutic zones may be characterized by minimum non-symptomatic, mixed symptomatic, or different single symptomatic signals.

In all cases, each identified therapeutic zone is an interval of the day that overlaps, and possibly includes, a portion of the window of time of the associated the risk profile. The one or more therapeutic zones represent therapeutic root cause of adjacent risk profiles and may be assessed by looking at a time window adjacent immediately prior to, and potentially overlapping with, the risk profile(s). Taken together, the identified therapeutic zones define time windows (i.e., intervals of the day) over which addressable portions of the glycemic risk profile can be mitigated, as described in more detail herein.

At 340, the importance of the therapeutically correlated zone is quantified. In some implementations, an importance value is determined of the therapeutically correlated zone. Thus, the importance of the one or more therapeutically correlated zones is quantified by the zone importance quantifier. The zone importance quantifier prioritizes which zone is more therapeutically significant or addressable. In some embodiments, the quantifier evaluates the magnitude of the risk, and may further consider the time of day and/or proximity of one risk profile to another risk profile (e.g., because in some cases two different risk profiles are related to each other as they are not isolated incidents and thus one impacts the other). The quantifier may use a mathematic function of the risk profile from 320, for example, the peak value of the glycemic risk profile, wherein that peak value could be equal to the importance of that therapeutic zone in one exemplary embodiment.

The quantifier may be derived from the glycemic risk in embodiments wherein only glucose data is available. However, if additional data is available, such as insulin, meals, and exercise, the quantifier may also consider these data in its evaluation. In some embodiments, priority could be assigned to therapeutic zones based on preferences of solving problems. For example, more significance to bolus issues vs. basal issues or vice versa may be assigned by the system or by the user. In some embodiments, the zone importance is informed by other factors such current basal-bolus insulin ratio, for example, 50% basal is already too high. In some embodiments, wherein insulin data is available and/or insulin strategy is determined as described in more detail elsewhere herein, the insulin strategy may be used to prioritize the therapeutically correlated zones.

In some embodiments, the quantifier assesses the opportunity for reducing risk for each of the one or more zones based on candidate changes to therapy, described in more detail elsewhere herein (e.g., using replay analysis), wherein the zone importance quantifier prioritizes therapeutic zones based on the opportunity to decrease the risk profile of one zone compared to another zone.

In some embodiments, systems and methods described herein may determine and apply an analysis of the credibility of the data prior to determining one or more of the data processing steps described herein. For example, the risk profiles derived by the glycemic risk profiler are based on data above a particular credibility level. In other words, credibility goes into the objective function of the risk profile. An example of credibility analysis and application is described in U.S. application Ser. No. 17/096,785, entitled "Joint state estimation prediction that evaluates differences in predicted vs. corresponding received data", filed Nov. 12, 2020, inventor Stephen D. Patek, which is incorporated by reference herein in its entirety.

At 350, numerical, alphanumerical, and/or graphical information based on the quantified importance of the therapeutically correlated zones is outputted. Thus, the therapeutic zone report generator outputs numerical, alphanumerical, and/or graphical information based on the quantified importance of the therapeutically correlated zones. In one embodiment, a visualization of the correlated zones are simply output onto a report. In other embodiments, behavioral and/or therapeutic changes to the therapeutic zone of time to decrease the single symptom in the identified recurring time window are identified and outputted.

In one example, when a hyperglycemia risk profile occurs in the middle of the day, e.g., the risk profile value is above a hyperglycemia risk threshold from a time zone of noon, and without hypoglycemia around it, then therapeutic zones immediately preceding (and possible overlapping) the noon to 4 PM time window could be assessed. In this case, time of day could also be an optional input and the possible root cause(s) may be analyzed using a look up table, decision tree, or the like, suggesting two reasons for hyperglycemia risk: 1) insufficient lunchtime bolusing (e.g., bolus parameters may be off, patient may be underestimating carbohydrate intake, or patient may not be bolusing at all, etc.); or 2) insufficient basal. Given the two possible root causes in this example, the report may describe two possible therapeutic issues to address 1) or 2).

Consider another example where hypoglycemia risk is identified and associated therapeutic zone is assessed before noon every day. There are three possible root causes that may be outputted: 1) overaggressive basal in the morning; 2) over-bolused; and/or 3) bolusing too late (accounting for carbs too late).

In an example wherein consistent hypoglycemia is followed by hyperglycemia, a single therapeutic zone may be outputted with cause/effect association of zones. The report generator may mark times of day where adjustments could be made, for example hyperglycemia followed by hypoglycemia, recommending a basal change at one time of day or changing of bolus parameters affected another time of day. The recommendations could be prioritized based on user preference/setting, the quantifier, or other insights such as described in more detail elsewhere herein (e.g., relative improvement of candidate changes or patient's insulin strategy). In combination scenarios, wherein a singleton zone represents therapeutically connected hypoglycemic and hyperglycemic zones, multiple combinations may be analyzed in view of impact on glycemic risk profile.

The output may be in the form of a user interface type report, may be sent to a connected insulin pump or insulin pen, or may be fed to into a bolus calculator. For example, a therapeutic zone associated with a time of day wherein changes to a carb ratio for meal boluses have been identified (and possibly confirmed/validated by user), the bolus calculator may be automatically programmed with a new carb ratio. Other recommendations may be more behavioral in nature, for example, a recommendation to bolus at an earlier time (e.g., before meal).

The report generator may generate and output a graphical representation of risk profiles, the therapeutically correlated zones, and/or their relative importance for visual inspection. Additionally or alternatively, a natural language generator or text generator may be used to communicate risk profiles, the therapeutically correlated zones, and/or their relative importance.

Figure 7:
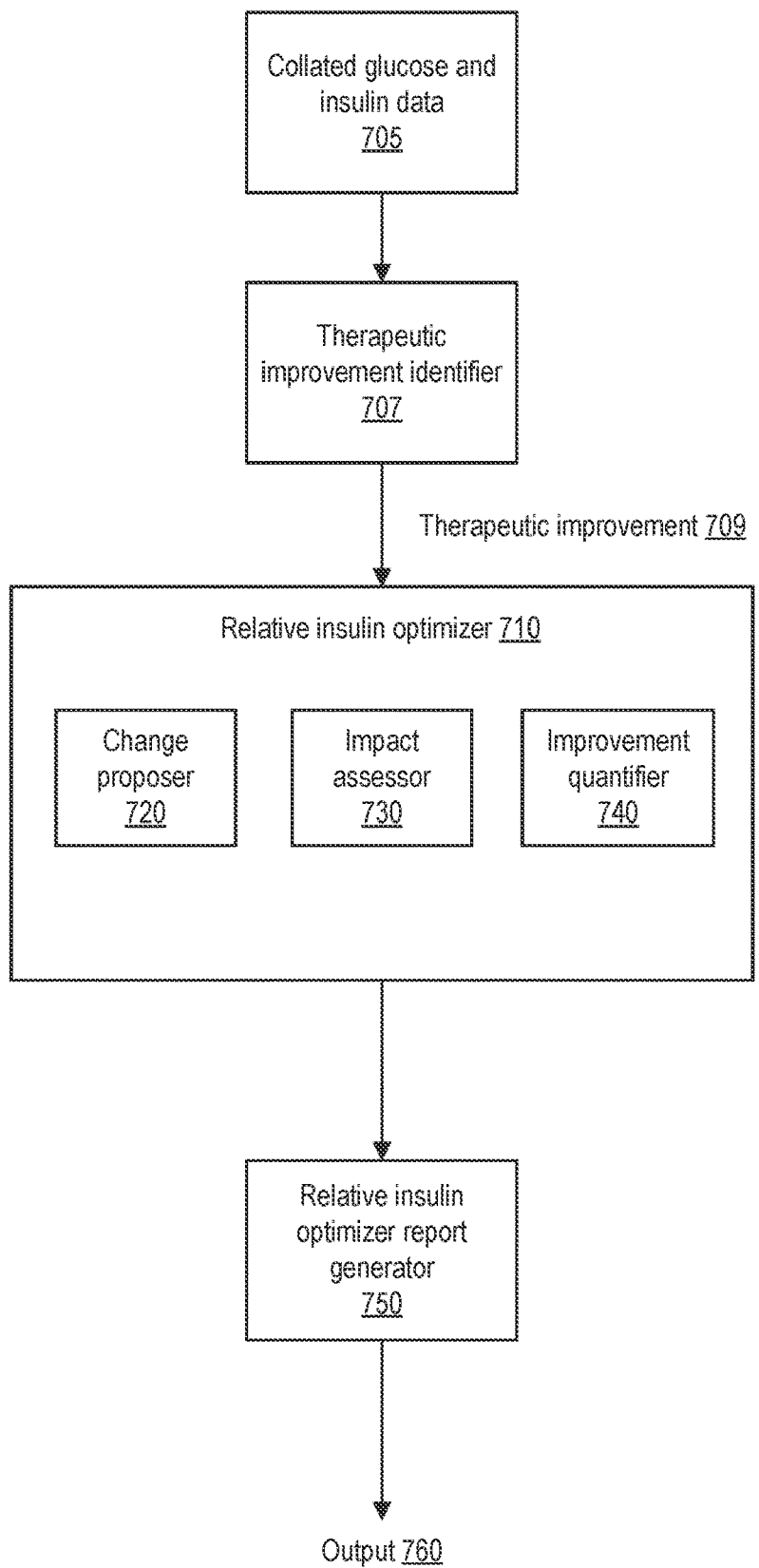
FIG. 7 is a system diagram of an implementation of a relative insulin optimizer.

FIG. 7 is a system diagram of an implementation of a relative insulin optimizer 710, which provides a general framework for the insulin optimization in the systems and methods described herein.

Blood glucose and insulin data are received (e.g., from the glucose monitor 120, the patient 140, the activity monitor 150, and/or the smartphone 160, in some implementations) and collated as needed depending on their sourcing, into collated glucose and insulin data 705.

The therapeutic improvement identifier 707 evaluates the collated glucose and insulin data 705 to identify areas for therapy optimization in a patient's diabetes management routine. In some embodiments, the identifier 707 may comprise a user selection from a clinician or patient (e.g., wherein a user identifies a specific therapy or time of day to be optimized). The user may select a particular mealtime (e.g., lunch), a specific time of day (e.g., upon waking in the morning), a particular setting (e.g., carb ratio), or the like. Any parameter or behavior that affects insulin therapy may be selected. In some embodiments, the therapeutic improvement 709 is identified by an algorithm, such as the therapeutic zone identifier 210 described with respect to FIG. 2; however, other algorithms for identifying areas for improvement are also possible as may be appreciated by one skilled in the art.

Based on the therapeutic improvement 709 identified, the relative insulin optimizer 710 proposes candidate changes to the therapy, assesses the impact of those changes, and quantifies the improvement associated with those changes.

The change proposer 720 proposes the candidate changes to insulin therapy such as percentage-wise changes to basal and/or bolus in a particular time window (e.g., zone or zone group).

The impact assessor 730 assesses impact of candidate therapy changes by estimating the impact to the risk profile of the historical glucose values.

The improvement quantifier 740 quantifies improvement of candidate therapy changes, for example, based on a percentage improvement/change in blood glucose outcome metrics.

The relative insulin optimizer report generator 750 provides an output 760, such as outputting candidate therapy change to a user (clinician, patient, or connected device/system).

Figure 8:
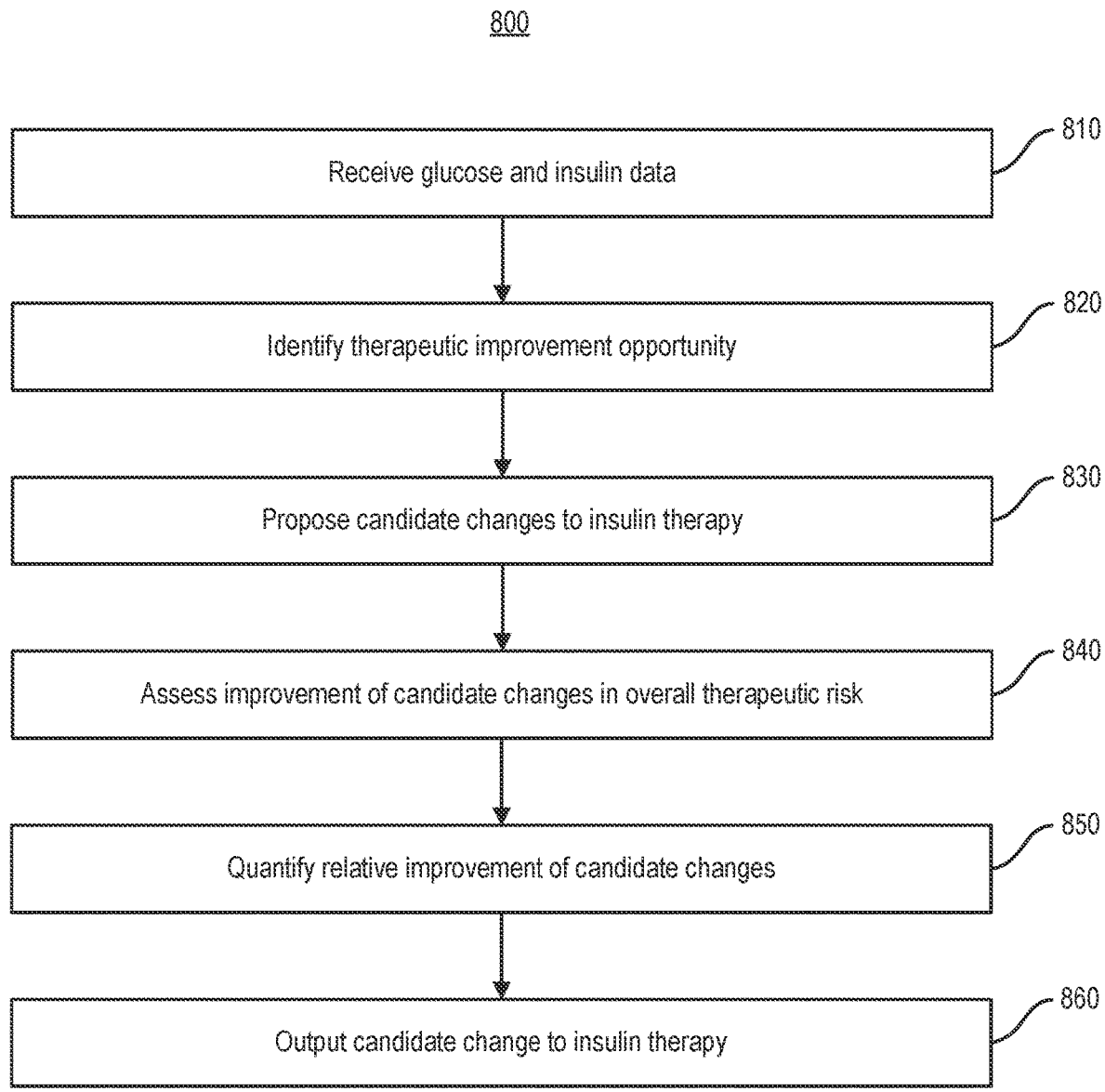
FIG. 8 is a flow diagram for a method of selecting, assessing, and impacting candidate insulin therapy changes for a patient.

FIG. 8 is a flow diagram for a method 800 of selecting, assessing, and impacting candidate insulin therapy changes for a patient. The methods receive glucose and insulin data received from the patient and/or a connected device to run optimization algorithms for improved insulin therapy based on quantified improvements associated with candidate changes to the insulin therapy. In one example, using glucose and insulin delivery data, using a replay predictive function, the effects of percentage changes to basal and/or bolus insulin in the identified therapeutic zones are analyzed.

Figure 9A:
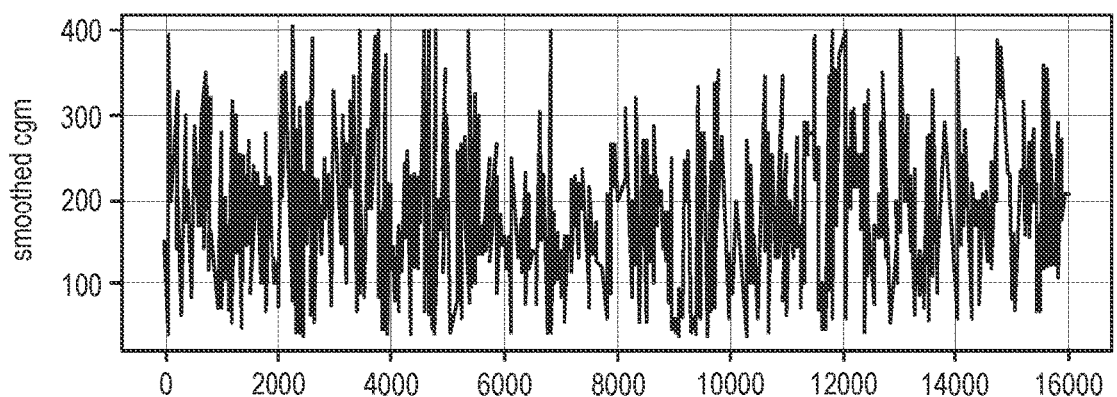
FIGS. 9A and 9B are graphs showing glucose and insulin data, respectively, for a patient over a period of time.
Figure 9B:
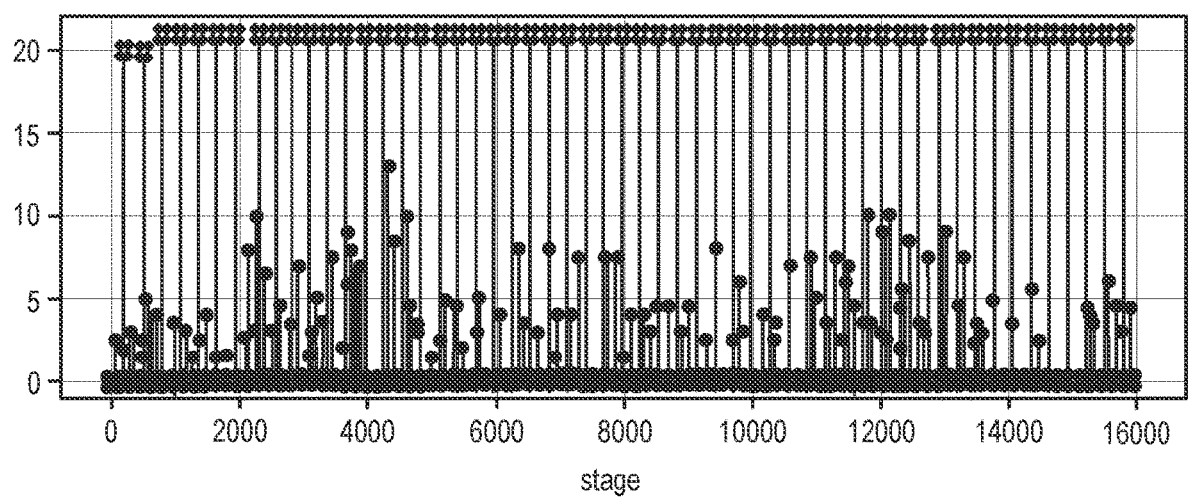
Figure 10:
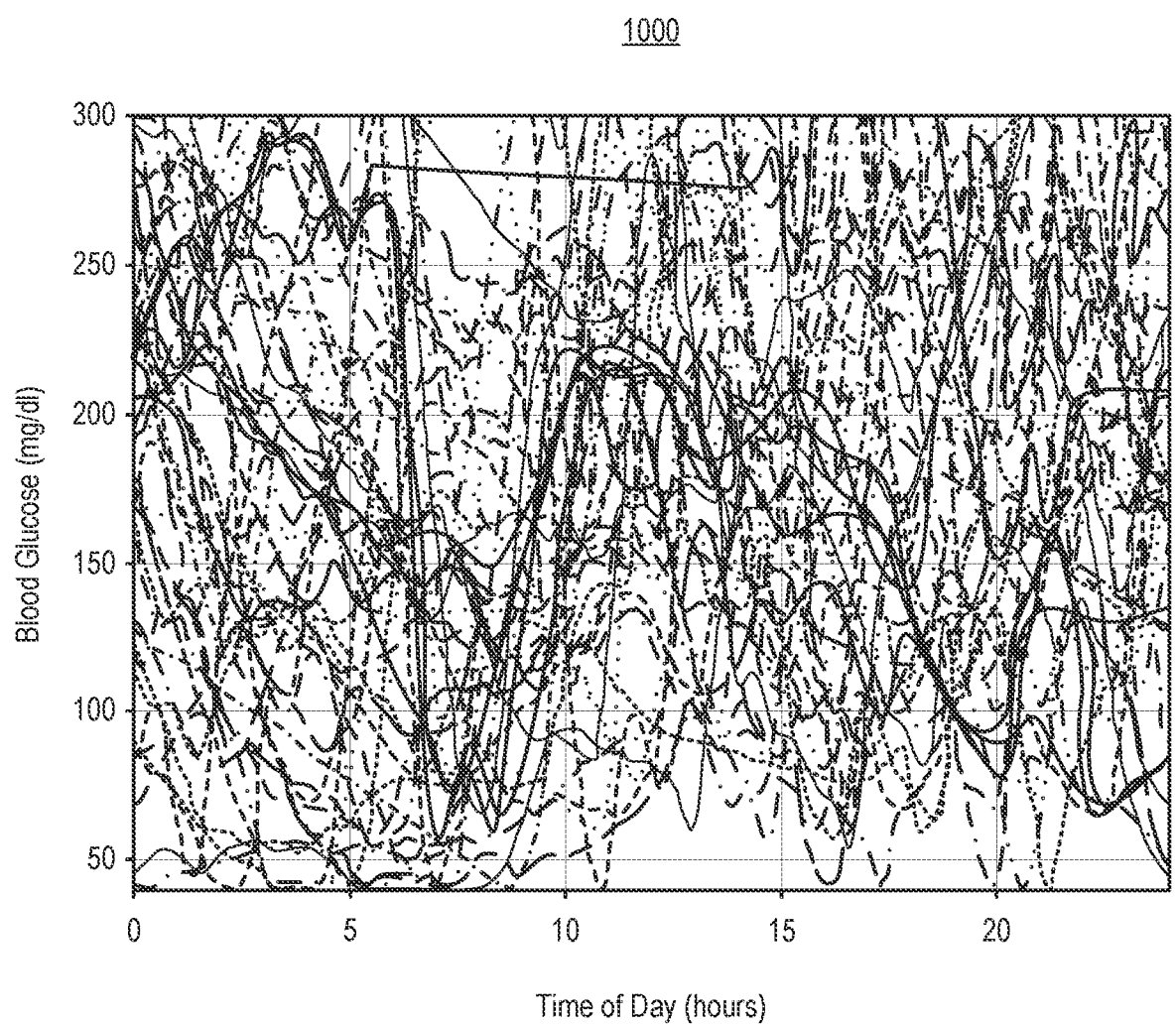
FIG. 10 is a plot showing a visualization of CGM data overlaid for each 24 hour day.
Figure 11:
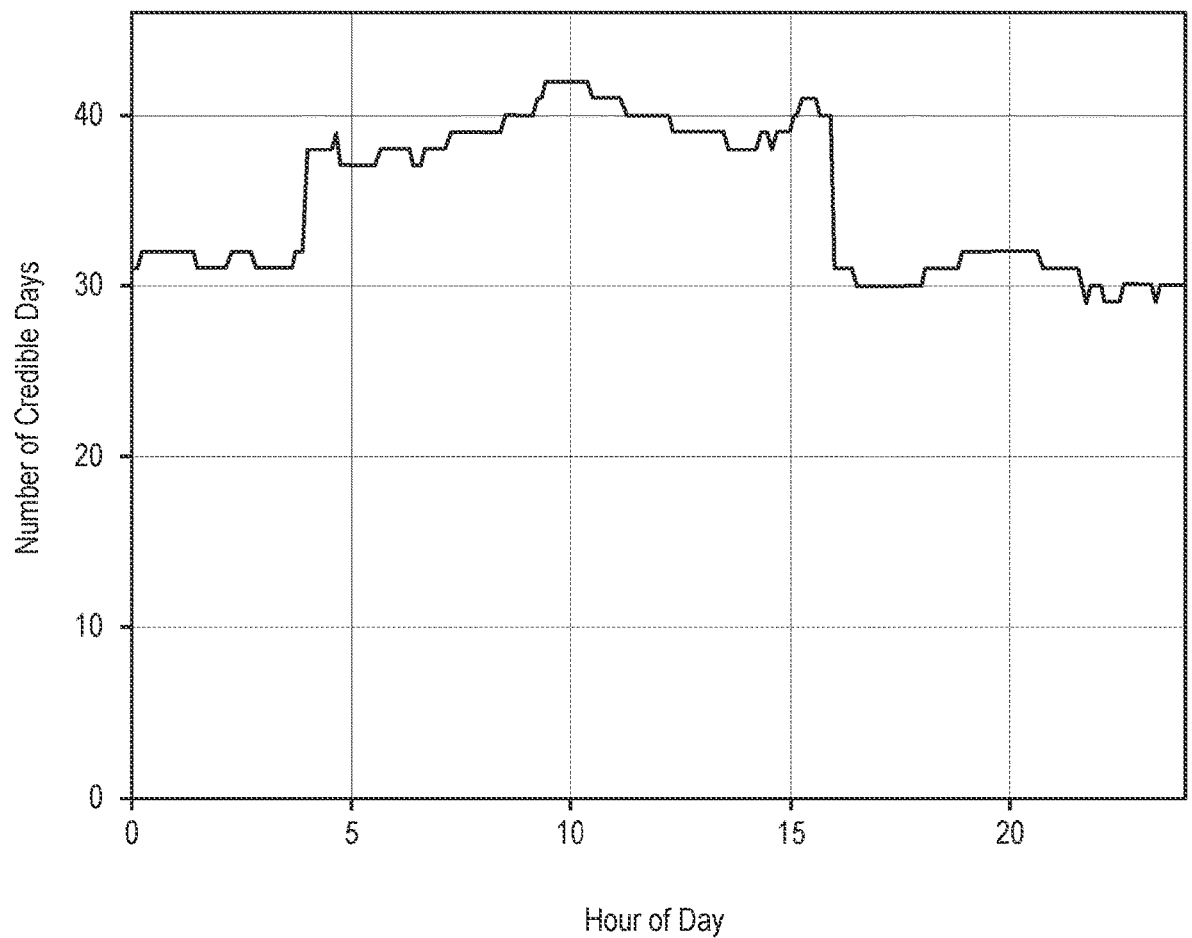
FIG. 11 is a graph showing credibility of the CGM and insulin data as a function of time of day for the data shown FIGS. 9A, 9B, and 10.

At 810, glucose and insulin data are received from a patient and/or connected system/device (e.g., from the glucose monitor 120, the patient 140, the activity monitor 150, and/or the smartphone 160, in some implementations). FIGS. 9A and 9B are graphs 900, 950 showing glucose and insulin data, respectively, for a patient over about 54 days. FIG. 10 is a plot 1000 showing a visualization of all CGM data overlaid for each 24 hour day. FIG. 11 is a graph 1100 showing credibility of the CGM and insulin data as a function of time of day for the data shown in the graphs immediately above.

At 820, a therapeutic improvement opportunity is identified as described in more detail elsewhere herein. In some embodiments, the therapeutic improvement opportunity identification may comprise a user selection from a clinician or patient (e.g., wherein a user identifies a specific therapy or time of day to be optimized). The user may select a particular mealtime (e.g., lunch), a specific time of day (e.g., upon waking in the morning), a particular setting (e.g., carb ratio), or the like. Any parameter or behavior that affects insulin therapy may be selected. In some embodiments, the improvement is identified by an algorithm, such as the therapeutic zone identifier described in more detail elsewhere herein, however other algorithms for identifying areas for improvement are also possible as may be appreciated by one skilled in the art.

Figure 12:
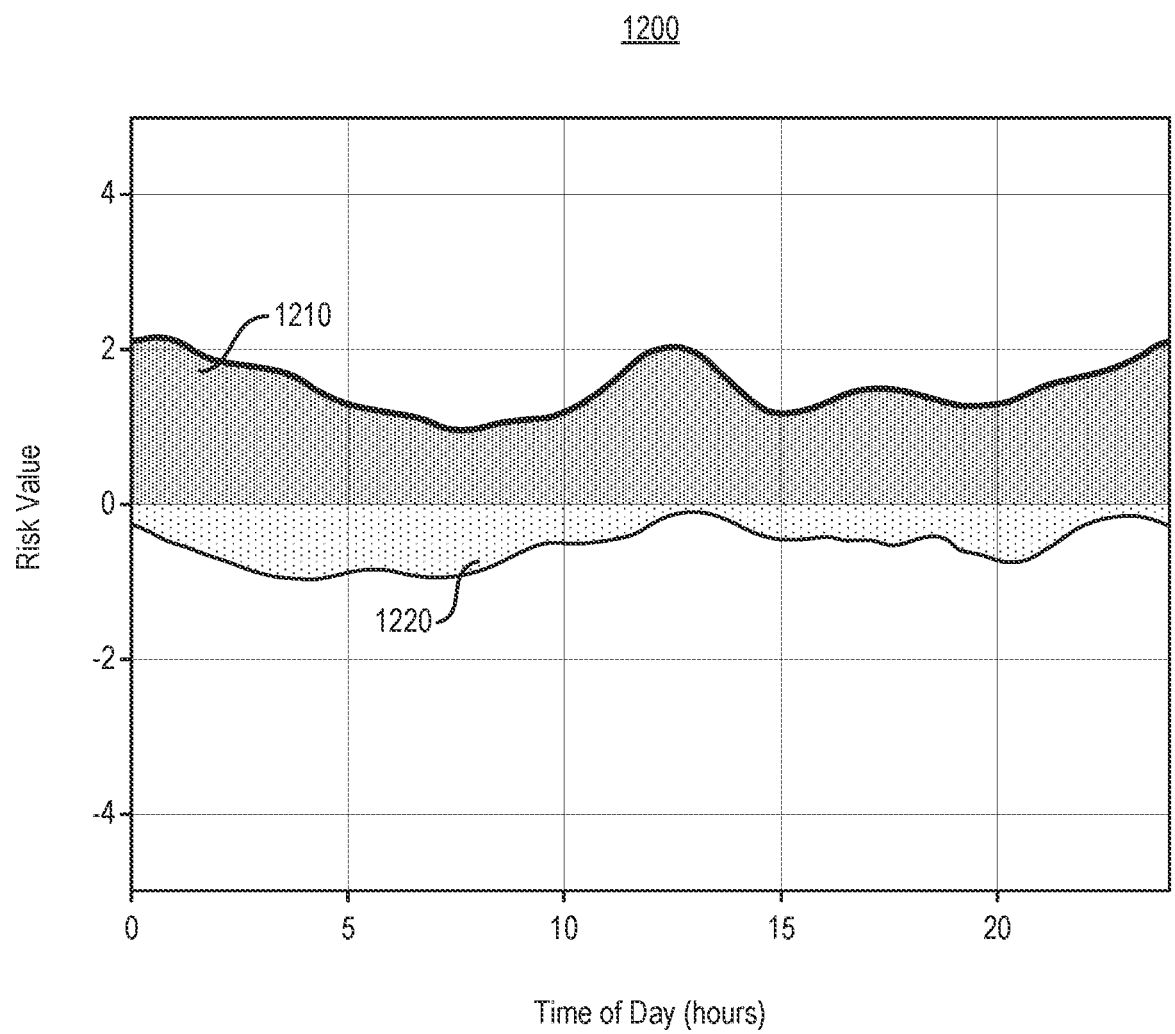
FIG. 12 is a chart that shows a risk profile for a patient over a window of time in some embodiments.

FIG. 12 is a chart 1200 that shows a risk profile for a patient over a window of time in some embodiments. The area 1210 above the zero line represents hyperglycemia, and the area 1220 below the zero line represents hypoglycemia as a function of time of day.

Figure 13A:
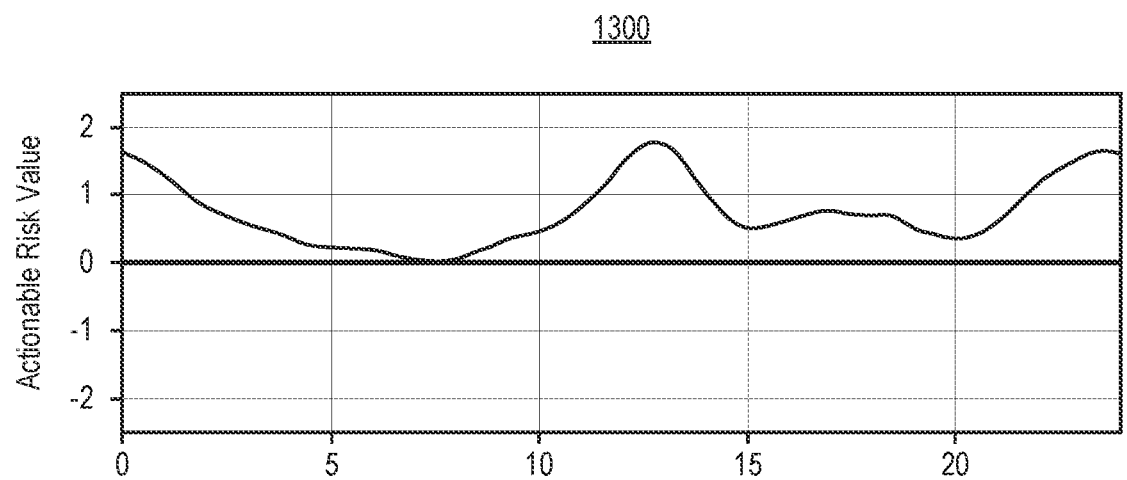
FIGS. 13A and 13B are charts that show actionable and unactionable risk, respectively, as a function of time of day.
Figure 13B:
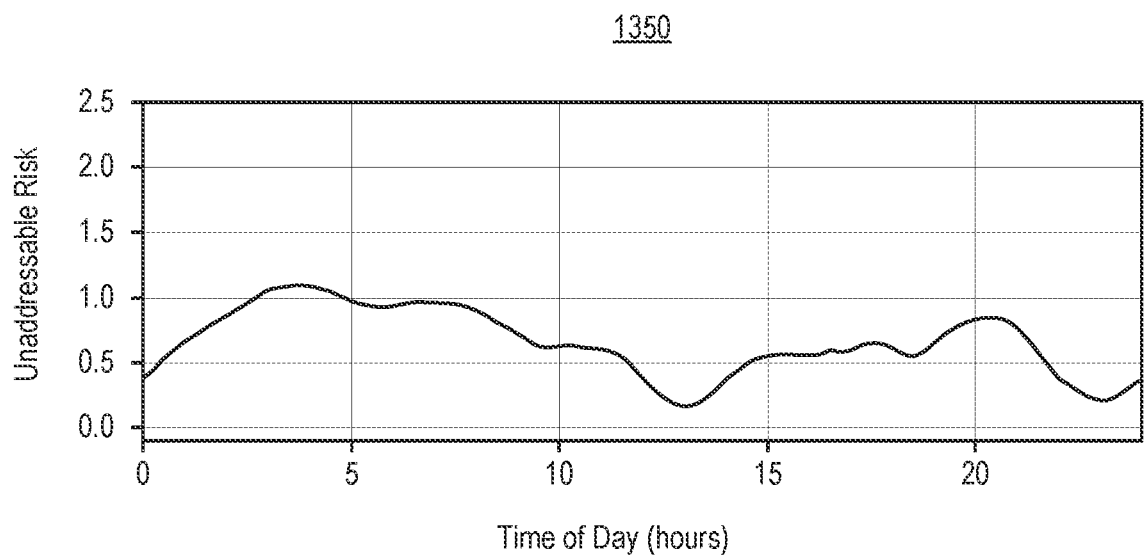

FIGS. 13A and 13B are charts 1300, 1350 that show actionable and unactionable risk, respectively, as a function of time of day. At around 13 hours (about 1 pm, just after lunch), a peak of actionable hyperglycemia risk exists while at the same time of day the level of unaddressable risk is low.

Figure 14:
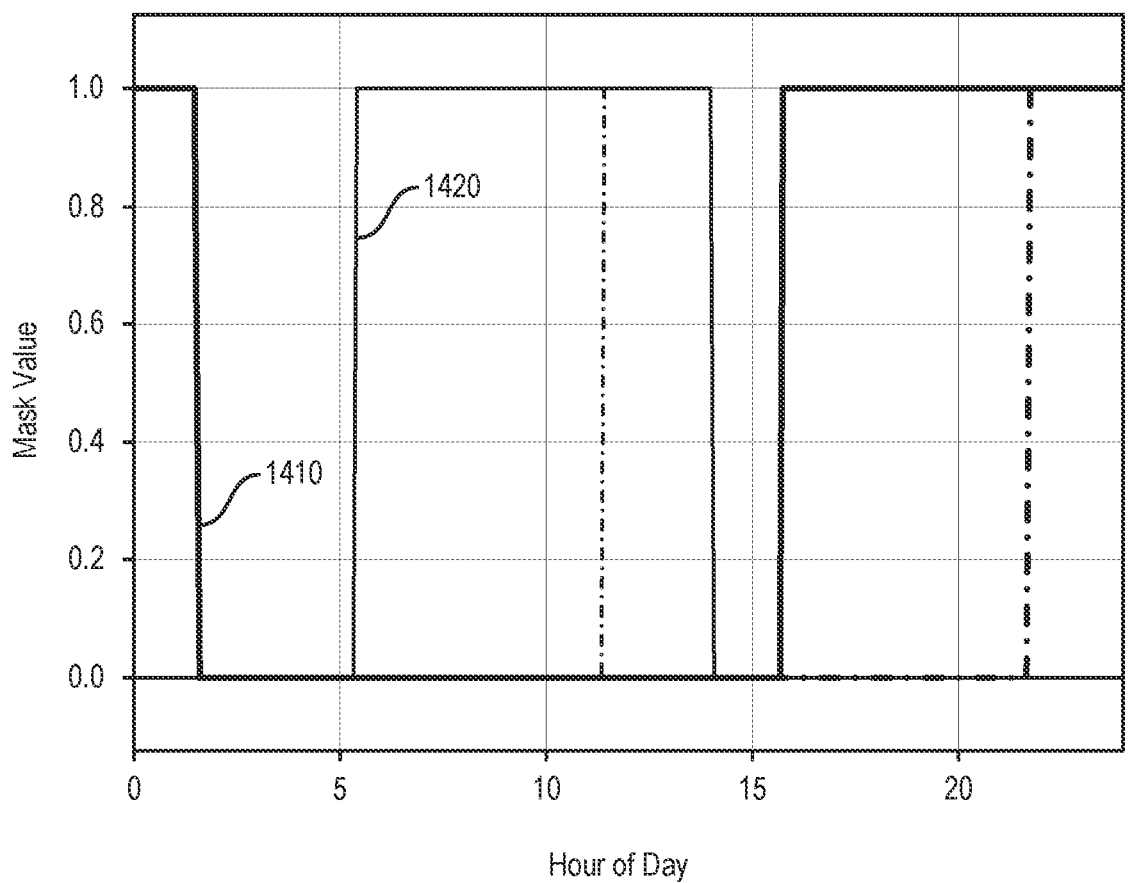
FIG. 14 is a chart, for an embodiment of the invention, that illustrates glycemic risk profiles and corresponding therapeutic zones determined from the risk profiles described with reference to FIGS. 12, 13A, and 13B.

FIG. 14 is a chart 1400, for an embodiment of the invention, that illustrates glycemic risk profiles and corresponding therapeutic zones determined from the risk profiles described with reference to FIGS. 12, 13A, and 13B. The lines 1410 represent the risk profiles and the lines 1420 represent the corresponding therapeutic zones. In this example, noon-2 pm shows actionable hyperglycemia risk indicating 10 AM-noon would be a candidate window to change to the insulin therapy.

At 830, candidate changes to insulin therapy are proposed (e.g., determined) during the therapeutic zone. Candidate changes to insulin therapy may comprise percentage increases or decreases to bolus or basal therapy and/or may include changes to insulin delivery parameters associated with the bolus or basal therapy.

Once the therapeutic zone is identified, candidate changes to therapy can be proposed directly in terms of, for example, carb ratios, correction factors, basal rates, and/or profiles thereof. One skilled in the art may appreciate that any parameters used in diabetes management that affects diabetes outcomes may be candidates for change. Parameters may be specific to insulin pumps, bolus calculators or any value associated with insulin therapy whether on type 1 or type 2 single or multiple daily injection therapy, insulin pen therapy, insulin pump therapy, artificial pancreas therapy, beta cell therapy, and/or any aspect(s) thereof.

In some implementations, basal dose sensitivity (percentage change basal doses and/or basal rates) are candidate changes. In some embodiments, candidate changes may include percentage change to basal or bolus doses in therapeutic zones. Compound changes and/or combination changes may also be proposed, for example, two-factor sensitivity (e.g., differentiated recommendations for basal vs. bolus). Time of day is also a factor that may be proposed for basal rates in some embodiments.

At 840, the improvement in overall therapeutic risk based on the candidate changes is assessed (e.g., determined). In some embodiments, a replay-predictive function, such as described in U.S. application Ser. No. 17/096,785, entitled "Joint state estimation prediction that evaluates differences in predicted vs. corresponding received data", filed Nov. 12, 2020, inventor Stephen D. Patek, which is incorporated by reference herein in its entirety, is performed to estimate the impact of the candidate changes at the therapeutic zones on historical glucose, and the risk profiling function is run to determine a new risk profile based on the candidate changes. For example, percentage changes (5%, 10%, etc.) to historic boluses and/or basal rates are replayed during therapeutic zones and resulting risk profiles are re-assessed.

At 850, the relative improvement of the candidate changes may be quantified. In one embodiment, the risk profile values are compared to quantify improvement.

At 860, the candidate change(s) to insulin therapy that provided the most optimized risk profile(s) is outputted. The output may be in the form of a graph illustrating the candidate change and/or optimized risk output to a user interface or connected device, such as a clinician report or connected bolus calculator. Additionally or alternatively, the output may be provided by a natural language processor to describe the candidate change and optimized risk outcome. The output may identify which therapeutic zones or zone groups have been optimized and, in some embodiments a text generator may be used to communicate the result(s).

Although diabetes data associated with type 1 diabetes has been illustrated and described herein, the systems and methods may be applicable to type 2 diabetes herein such as for basal titration acceleration, to identify and assess the risk of more or less aggressive type 2 injections (in terms of medication type, medication dosage, and/or time of injection).

Figure 15:
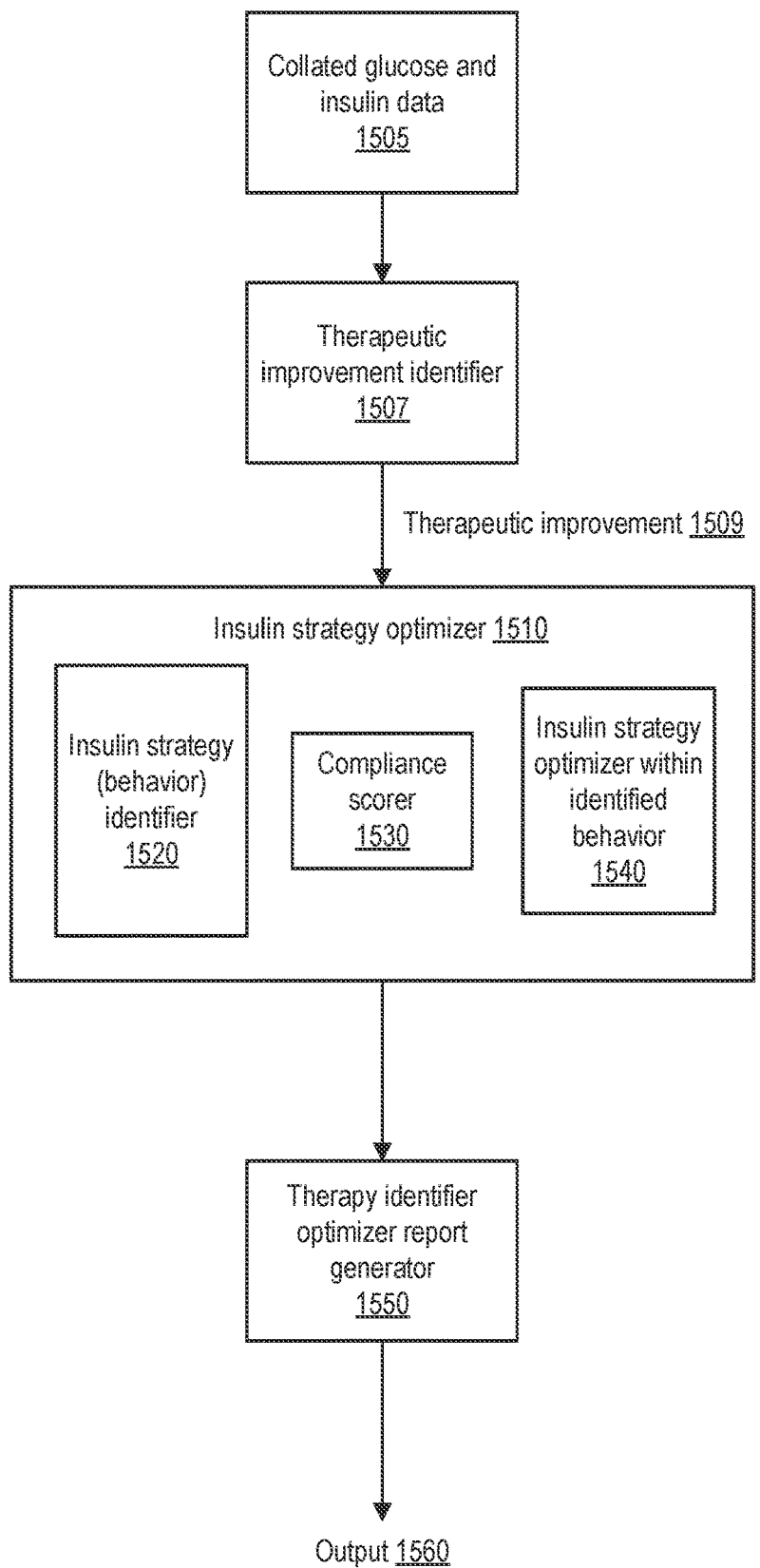
FIG. 15 is a system diagram of an implementation of an insulin strategy optimizer.

FIG. 15 is a system diagram of an implementation of an insulin strategy optimizer 1510, which provides a general framework for the insulin optimization in the systems and methods described herein.

Blood glucose and insulin data are received (e.g., from the glucose monitor 120, the patient 140, the activity monitor 150, and/or the smartphone 160, in some implementations) and collated as needed depending on their sourcing, into collated glucose and insulin data 1505.

The therapeutic improvement identifier 1507 evaluates the collated glucose and insulin data 1505 to identify areas for therapy optimization in a patient's diabetes management routine. In some embodiments, the identifier 1507 may be a user selection from a clinician or patient (e.g., wherein a user identifies a specific therapy or time of day to be optimized). The user may select, for example, a particular mealtime (e.g., lunch), a specific time of day (e.g., upon waking in the morning), a particular setting (e.g., carb ratio), or the like. Any parameter or behavior that affects insulin therapy may be selected. In some embodiments, the therapeutic improvement 1509 is identified by an algorithm, such as the therapeutic zone identifier 210 described with respect to FIG. 2; however, other algorithms for identifying areas for improvement are also possible as may be appreciated by one skilled in the art.

Using the records of glucose, insulin, and other data, the insulin strategy optimizer 1510 determines: (1) whether the patient adheres to a known insulin strategy (e.g., "functional insulin therapy" with pre-meal boluses based on carb counts) and (2) analyzes the effect of percentage changes to the parameters of the identified insulin strategy (e.g., carbohydrate ratios, correction factors, basal rates/dose, etc.). In contrast to the prior art insulin optimizers that make assumptions about the patient's insulin strategy and/or require changes in the patient's behavioral insulin strategy, the systems and methods described herein identify the patient's current insulin dosing strategy from numerous different strategies to adapt the insulin therapy optimization to the patient's chosen behavioral insulin strategy matching their actual real-world strategy. Optimization focused on how the patient thinks about their insulin treatment (i.e., strategy) allows for more customized user recommendations, resulting in increased compliance and improvement.

Figure 16:
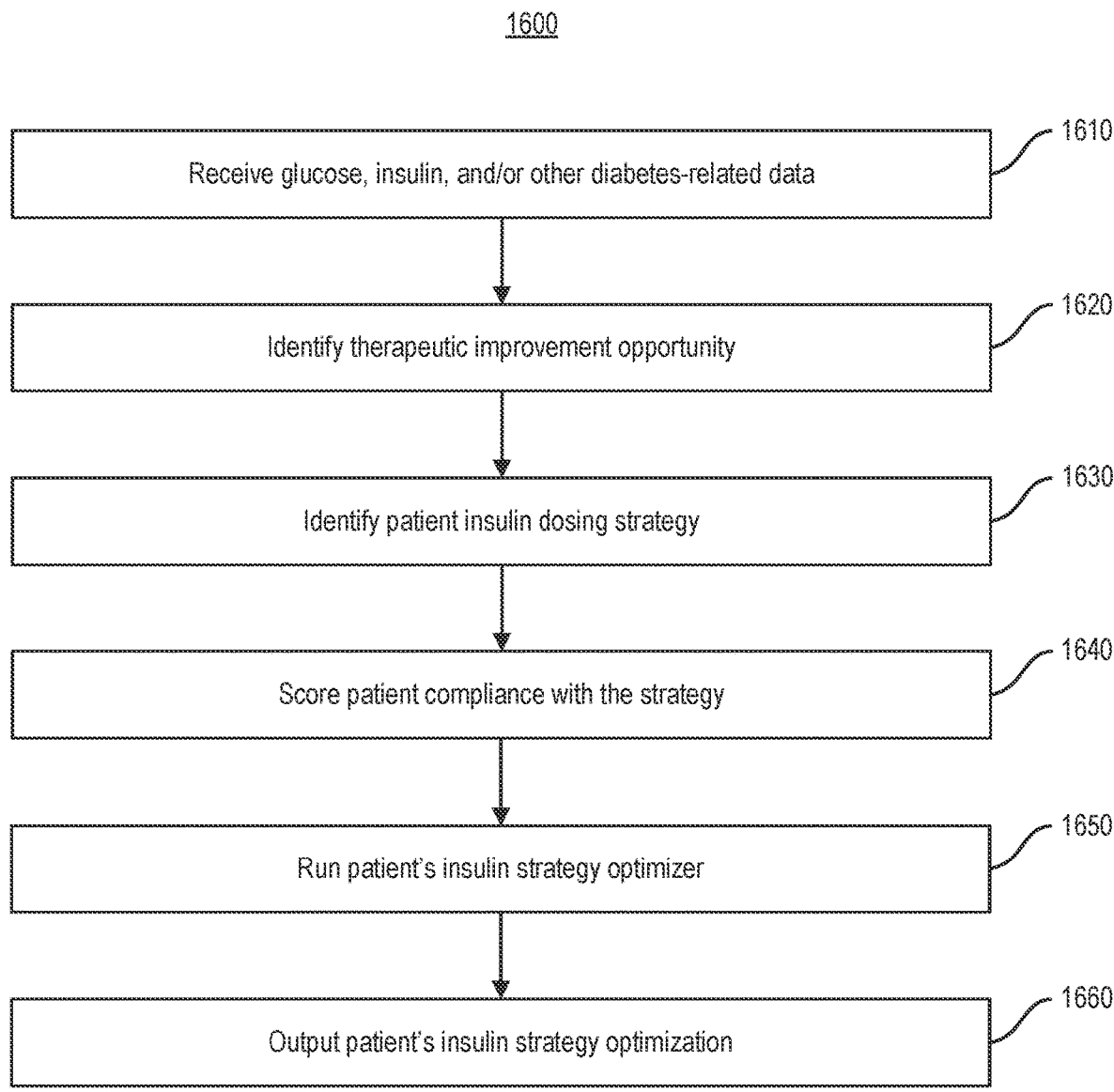
FIG. 16 is a flow diagram for a method of identifying, scoring, and optimizing a patient's insulin strategy.

FIG. 16 is a flow diagram for a method 1600 of identifying, scoring, and optimizing a patient's insulin strategy. The methods receive glucose, insulin and other diabetes-related data, such as meal or exercise data, from the patient and/or a connected device. From the patient data, behavioral patterns can be identified to determine how the patient prefers to manage their diabetes. With knowledge of the patient's insulin dosing strategy, changes to the amount and/or timing of strategy-specific parameters can be evaluated and recommended as described in more detail herein.

At 1610, glucose, insulin, and/or other diabetes-related data is received (e.g., from the glucose monitor 120, the patient 140, the activity monitor 150, and/or the smartphone 160, in some implementations). The other diabetes-related data may include meal information, such as, for example, specificity and/or timing of meals, general or specific sizing of meals, carbohydrate estimates, composition information, and the like. Additionally or alternatively, exercise information may be provided to include, for example, type of exercise, duration, intensity, heart rate, calories burned, and the like. Diabetes-related data may come from a connected device and/or be self-reported. The data may be collated with glucose and insulin data as appreciated by one skilled in the art.

At 1620, a therapeutic improvement opportunity is identified as described in more detail herein. In some embodiments, the therapeutic improvement opportunity identification may comprise a user selection from a clinician or patient (e.g., wherein a user identifies a specific therapy or time of day to be optimized). The user may select a particular mealtime (e.g., lunch), a specific time of day (e.g., upon waking in the morning), a particular setting (e.g., carb ratio), or the like. Any parameter or behavior that affects insulin therapy may be selected. In some embodiments, the improvement is identified by an algorithm, such as by the therapeutic zone identifier 210, however other algorithms for identifying areas for improvement are also possible as may be appreciated by one skilled in the art.

At 1630, the patient's insulin dosing strategy is identified. The insulin strategy identifier 1520 identifies the diabetes management/insulin strategy being implemented by the patient in practice as determined from the diabetes data (insulin data and meal data). The strategy identifier 1520 may comprise a series of questions for the patient or selections to be made by the patient. In some embodiments, the identifier 1520 identifies patterns in dosing and characterizes the patient's insulin strategy based thereon. The identifier 1520 may use the replay-predictive function (e.g., described in U.S. application Ser. No. 17/096,785, entitled "Joint state estimation prediction that evaluates differences in predicted vs. corresponding received data", filed Nov. 12, 2020, inventor Stephen D. Patek, which is incorporated by reference herein in its entirety) or the like, along with the other data relevant to dosing to attempt to reproduce the patient's historical insulin decisions in context.

By "insulin strategy" it is meant the behavioral methodology that the patient applies in diabetes management, including types of insulin pump usage, multiple daily injections, and type 2 therapies as may be appreciated by one skilled in the art.

As one example, the systems and methods identify the patient as a pump user and may further identify the type of usage of the pump, selected from: open loop (evaluates basal and/or bolus/timing), semi-closed loop, and closed loop (which may be further divided, for example, into artificial pancreas algorithm type A and artificial pancreas algorithm type B). Other insulin pump strategies may be identified as appreciated by one skilled in the art, including programmable basal and bolus settings, both in terms of timing and amount, as well as combination basal-bolus therapies recommended by particular programs or providers.

As another example, the systems and methods identify whether the patient boluses, and if so, what behavioral strategy is associated with their regular bolus pattern. One bolus pattern used by some patients includes a fixed time of day bolusing strategy (i.e., bolusing at specific times of day), meal-time bolusing, carb counting bolusers (e.g., wherein the patient regularly enters different carb amounts at most meals), non-carb counting bolusers (e.g., wherein the patient estimates (S/M/L)), pre-meal bolusing (dosing first and then titrating food), micro-boluser bolusing (e.g., bolusing more than x times per day on average (where x is greater than 5, 6, 7, or more)), and the like as is appreciated by one skilled in the art.

Other examples include sliding scale bolusing, wherein systems and methods identify whether the patient boluses responsive to BG above a certain range. Other philosophies for insulin management may be considered as may be appreciated by one skilled in the art.

At 1640, the strategy is optionally scored for patient compliance with that strategy. The insulin strategy scorer (compliance scorer) 1530 quantifies the patient's compliance with the identified insulin strategy, how strictly the patient adheres to the identified insulin strategy. The score is computed for the patient's degrees of compliance with the strategy, which may be used as a gate keeper to determine whether or how to proceed to the next step. For example, if the compliance score is above a given threshold level, then processing next step, else additional analysis, patient query, or feedback to a different algorithm (e.g., FIG. 8) may be performed.

At 1650, optimization is performed for the identified strategy. In other words, the optimization is limited by the bounds of the patient's preferred diabetes management regime without requiring behavior modification. While not wishing to be bound by theory, by optimizing insulin therapy informed by patient behavior, more efficient and effective therapy optimization may be achieved.

In general, the insulin strategy adapter (insulin strategy optimizer within the identified behavior 1540) adapts the insulin optimization/recommendation based on the selected insulin strategy and/or based on the score associated with the insulin strategy. In some embodiments, the optimization iteratively proposes percentage changes to the parameters of the strategy in a selected therapeutic zone or zone group, after which the improvement(s) may be quantified in a feedback loop fashion until a certain improvement is achieved and/or no more improvement through iterative change can be seen in the quantification.

In some embodiments, the optimization may use the replay-predictive function (e.g., described in U.S. application Ser. No. 17/096,785, entitled "Joint state estimation prediction that evaluates differences in predicted vs. corresponding received data", filed Nov. 12, 2020, inventor Stephen D. Patek, which is incorporated by reference herein in its entirety) to estimate the impact on historical BG. In these embodiments, the risk profiling function may re-run on each iterative optimization and the percentage improvement/change in BG outcome metrics assessed until a certain criteria is met.

At 1660, the optimized insulin strategy parameters are outputted to a user interface or a connected device e.g., via a therapy identifier optimizer report generator 1550. In an implementation, the therapy identifier optimizer report generator 1550 provides an output 1560, such as outputting candidate therapy change to a user (clinician, patient, or connected device/system). The output 1560 may be in the form of a graph illustrating the optimized insulin strategy parameters. In some implementations, one or more parameters may be output to a user interface or connected device, such as a clinician report or connected bolus calculator. Additionally or alternatively, the output may be provided by a natural language processor to describe the candidate change and optimized risk outcome. The output may identify which time windows have been optimized and, in some embodiments a text generator may be used to communicate the result(s).

Figure 17:
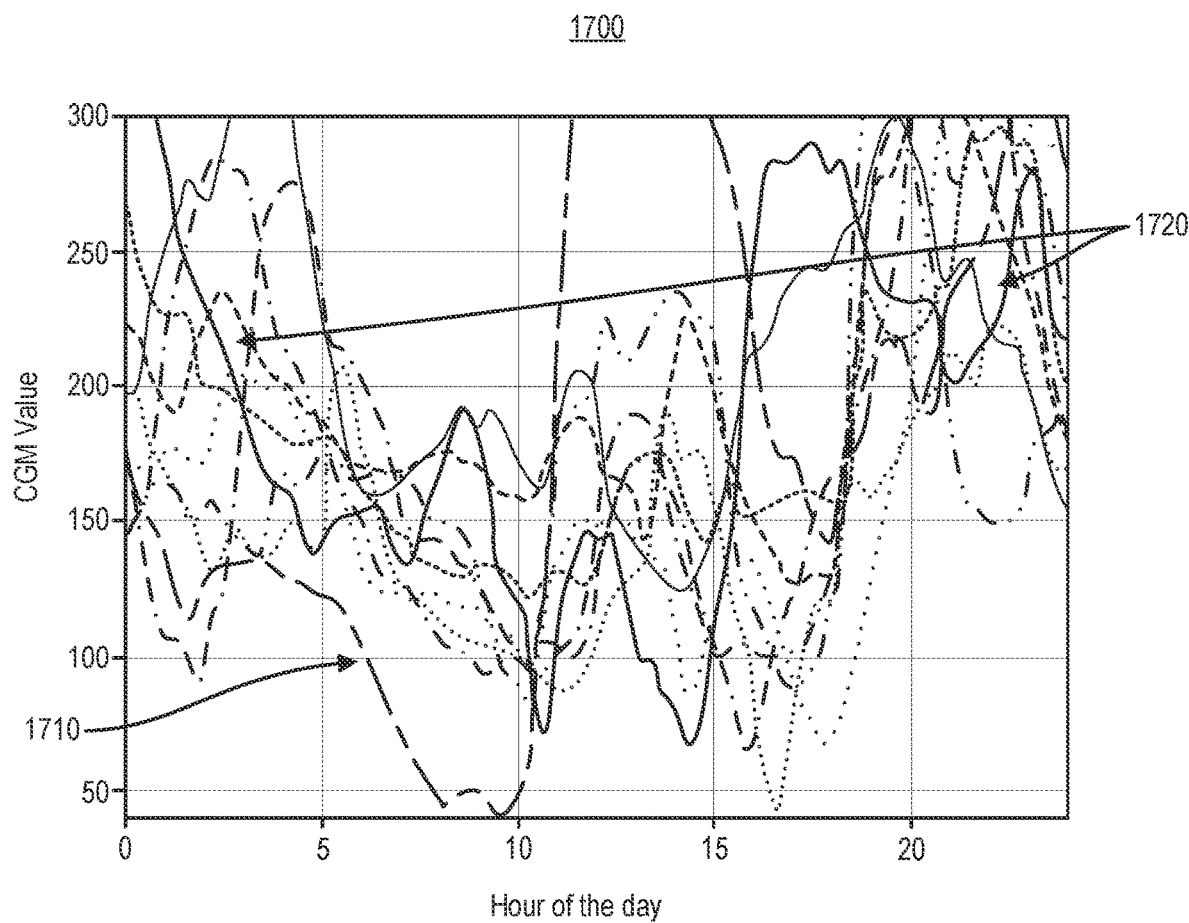
FIG. 17 is a chart that shows 10 days of CGM data for a patient.

An example of insulin strategy optimizer 1510 is now described on one data set from a patient with type 1 diabetes. In this example, historic CGM data was analyzed to identify nocturnal hyperglycemia as an addressable risk profile. FIG. 17 is a chart 1700 that shows 10 days of CGM data for the patient. Although there is one outlier day with mid-morning hypoglycemia and significant rebound on one day (indicated by line 1710), a systematic pattern of nocturnal hypoglycemia can be seen in the majority of the traces (indicated by lines 1720). This is a combination example wherein the replayer is built, therapeutic zones identified, strategic adjustments made (e.g., percentage change in strategic parameter (or sweep of parameters)) and then replayed to find optimal glycemic outcome.

Figure 18:
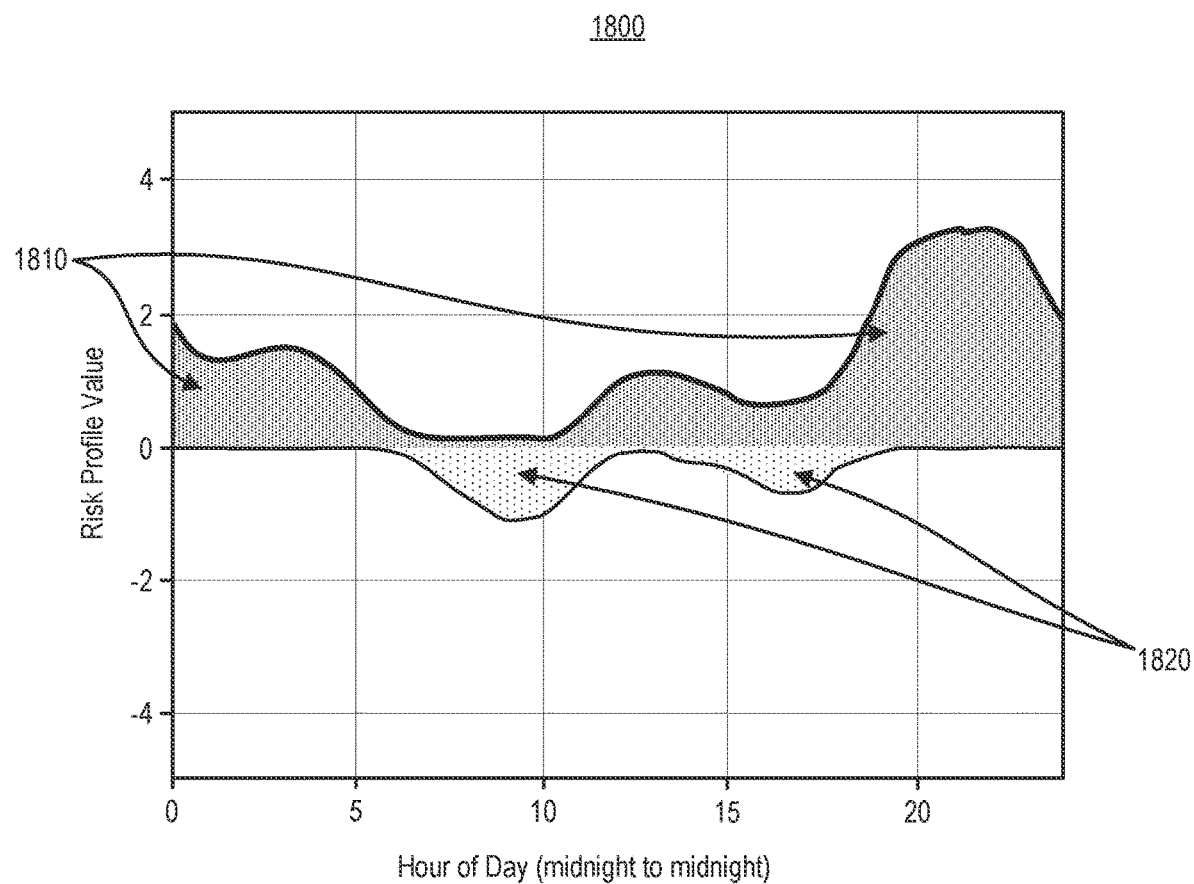
FIG. 18 is a chart that illustrates the risk profile function output from the analysis of the 10 days of CGM data shown in FIG. 17.

FIG. 18 is a chart 1800 that illustrates the risk profile function output from the analysis of the 10 days of CGM data show FIG. 17. The risk profile output confirms the consistent exposure to hyperglycemia overnight indicative of enhanced hyperglycemia risk (shaded region 1810 above the x-axis). Some exposure to daytime hypoglycemia is shown as hypoglycemia risk (shaded region 1820 below the x-axis). Accordingly, the therapeutic improvement opportunity is identified from the hyperglycemia risk profile above as nocturnal hyperglycemia especially during the time period wherein the risk profile value is above 2, about 1800 hours to about 2400 hours. This risk is addressable because there is no concurrent hypoglycemia adjacent to the nocturnal hyperglycemia.

Upon analysis of the concurrent insulin data (provided by basal and bolus data) and meal data (provided by acknowledged carbohydrate data), the patient is identified as using a functional insulin therapy (basal-bolus therapy), bolusing at times of acknowledged carbohydrates. From the data, the nominal parameters can be identified, including prevailing basal prescription and current correction factor and carbohydrate ratio programmed into the bolus calculator In this example, the insulin strategy optimizer utilizes the replay simulation (e.g., described in U.S. application Ser. No. 17/096,785, entitled "Joint state estimation prediction that evaluates differences in predicted vs. corresponding received data", filed Nov. 12, 2020, inventor Stephen D. Patek, which is incorporated by reference herein in its entirety). The replay simulates carbohydrates as historically acknowledged by the patient during data collection. Boluses are simulated only at times of acknowledged carbohydrates. Discordance between the replay simulation and historical data is expected because boluses are not simulated at times of historical boluses. Simulated doses are computed strictly according to the prevailing simulated BG, IOB (insulin on board), and acknowledged carbohydrates and the current prescription of carbohydrate ratio and correction factor. This may be referred to as compliant functional insulin therapy.

Figure 19:
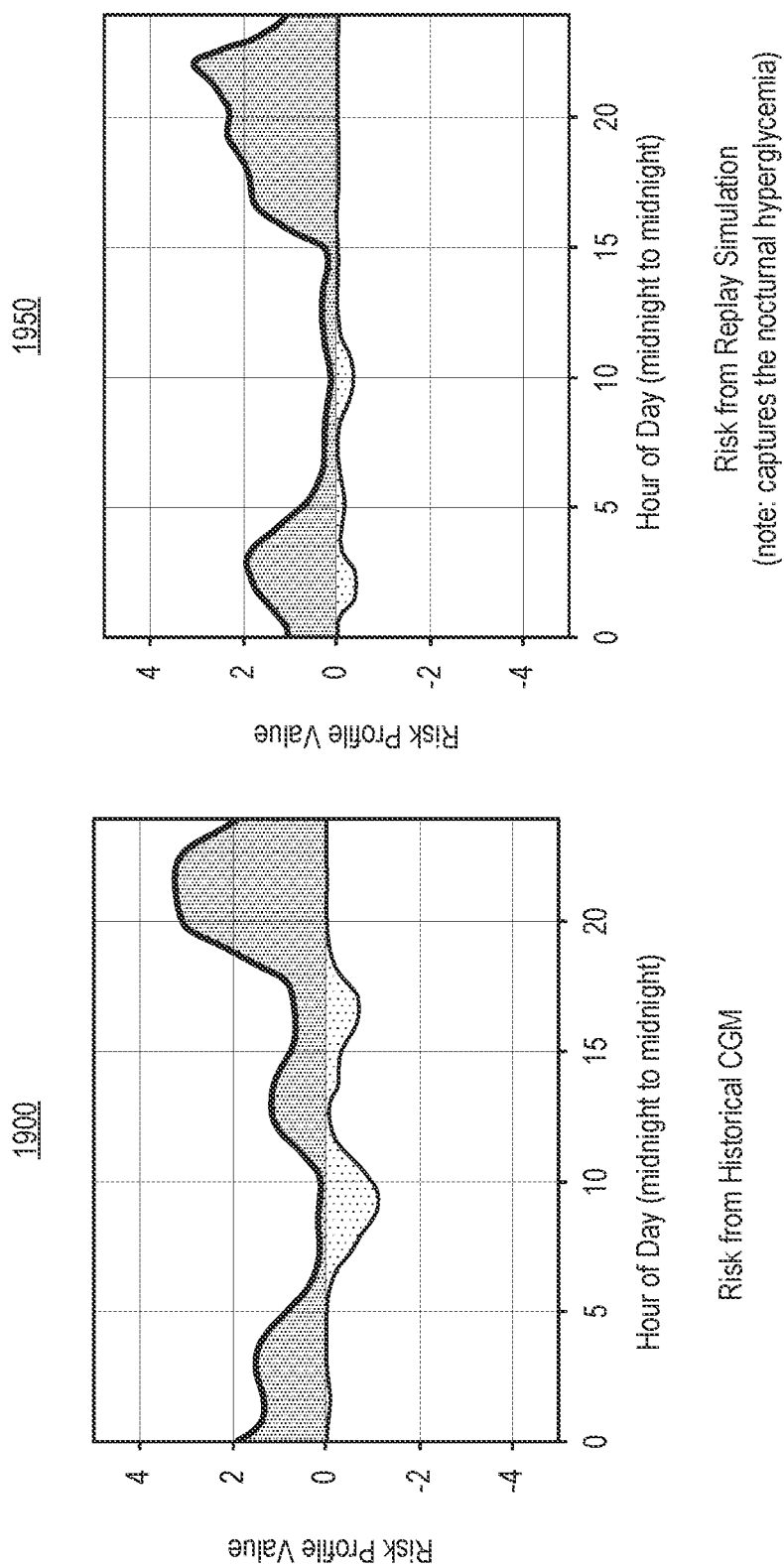
FIG. 19 are charts that illustrate a comparison of risk profiles from the historical data and from replay simulation.

FIG. 19 are charts 1900, 1950 that illustrate a comparison of risk profiles from the historical data and from replay simulation. Thus, for this example, one would only expect to see a close match between simulated CGM traces and historical CGM if the patient (1) eats exactly according to the carbohydrate announcements and (2) only boluses at meal times. In this example, historical boluses may be delayed and estimates of carbohydrates and insulin on board may be inaccurate. Patient compliance may be optionally scored here to determine compliance with the function insulin therapy.

Figure 20:
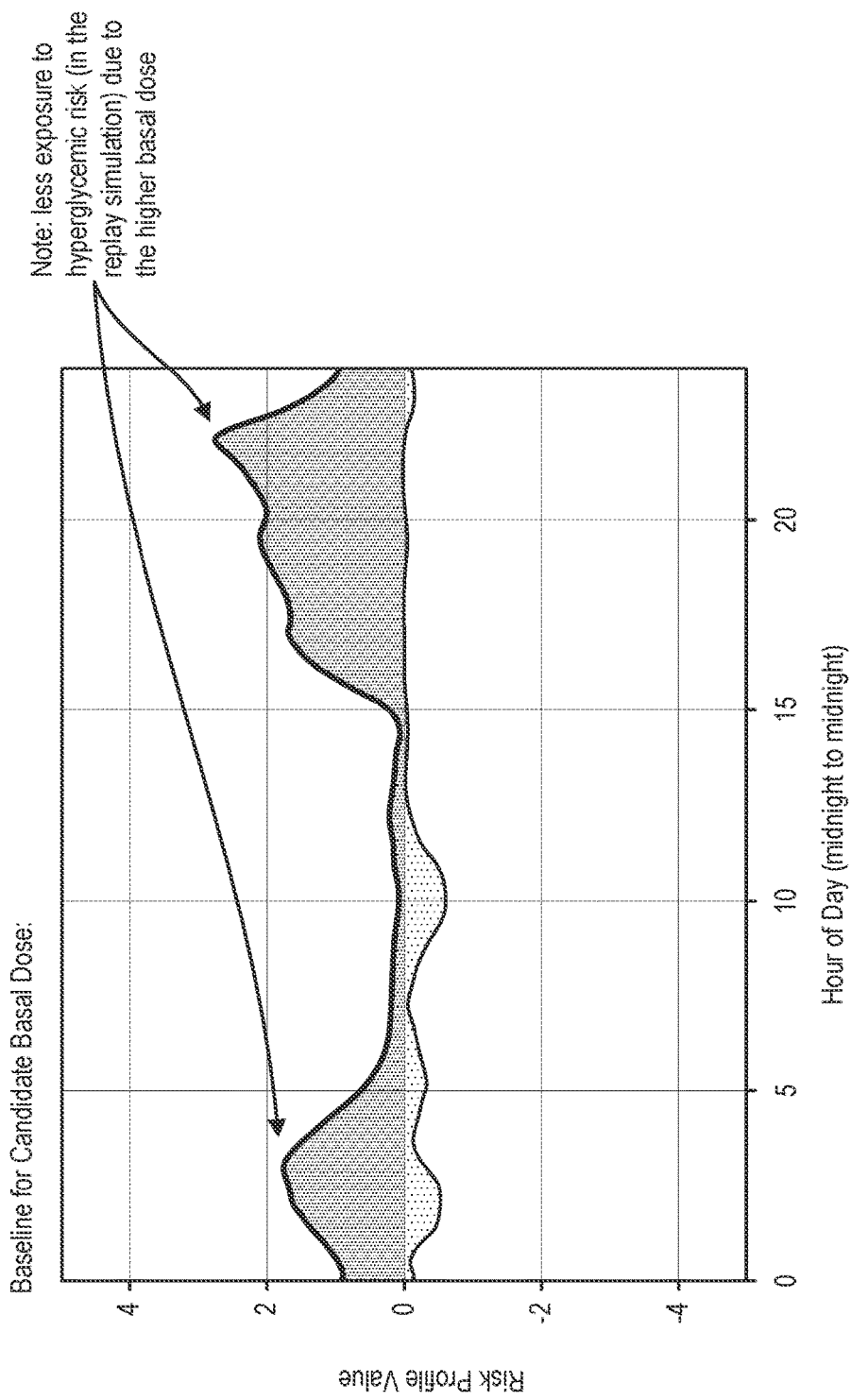
FIG. 20 illustrates a risk profile from a replay.

Next, replay simulations are run on the simulated CGM traces for a large number of candidate parameter settings, here using a reduced basal insulin dose. The parameters that do the most to minimize the patient's (replayed) exposure to hypoglycemic risk and hyperglycemic risk are stored for future reference. The risk profiles and therapeutic zones are re-run. FIG. 20 illustrates a risk profile 2000 from a replay.

Figure 21:
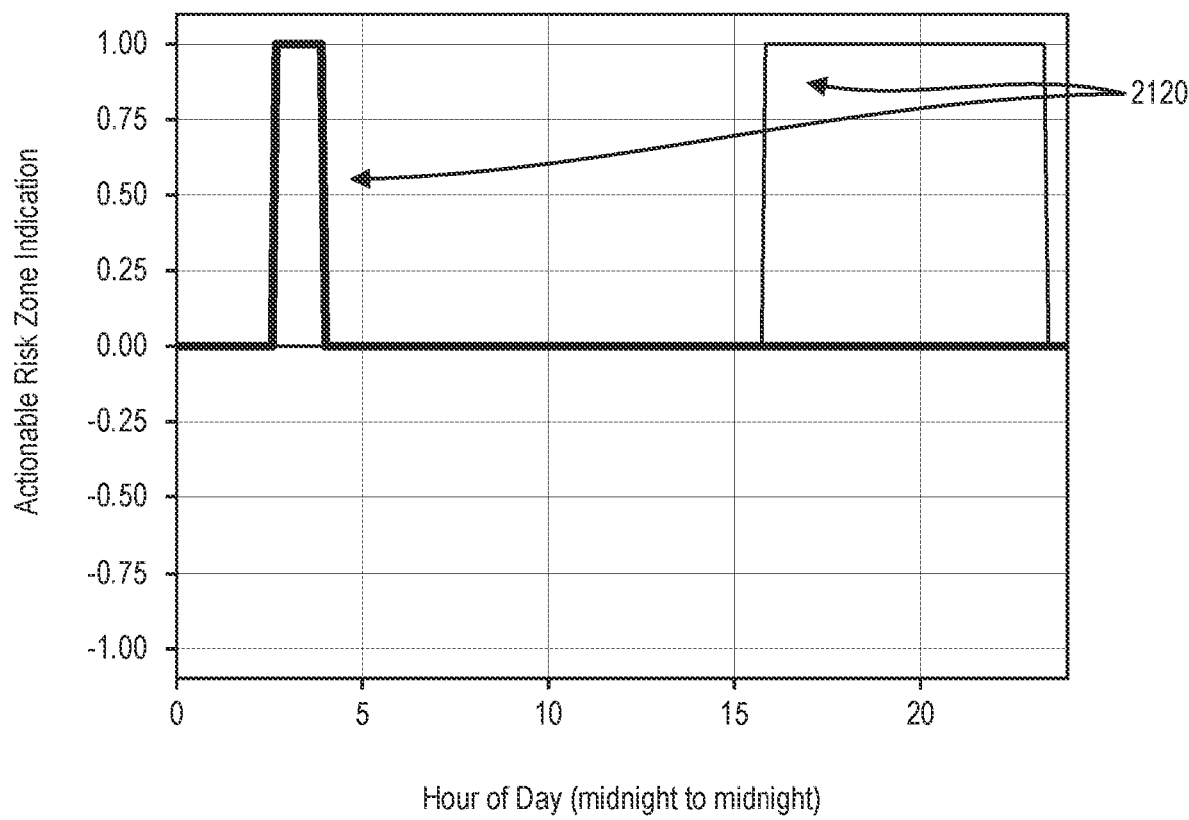
FIG. 21 is a chart showing two hyperglycemic risk profiles.
Figure 22:
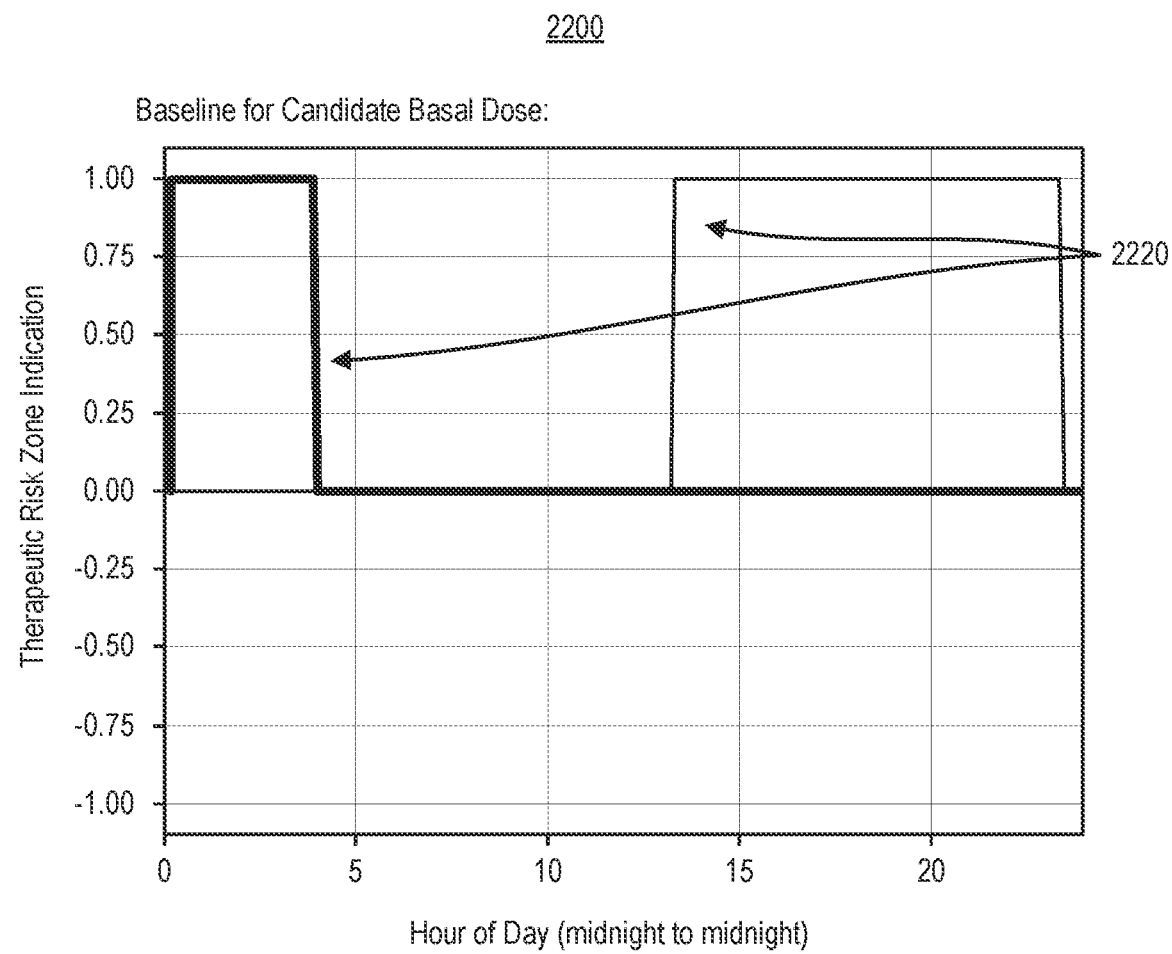
FIG. 22 is a chart showing two corresponding hyperglycemic therapeutic zones.

As an example, FIG. 21 is a chart 2100 showing two hyperglycemic risk profiles 2120. Similar to the nominal case, the zones are smaller because the higher basal done leads to less time with BG in the hyperglycemic range. As another example, FIG. 22 is a chart 2200 showing two corresponding hyperglycemic therapeutic zones 2220.

Further optimization can be provided for carbohydrate ratios and correction factors. Replay simulations are run for a large number of candidate parameter settings, here using an increased basal insulin dose. The parameters that do the most to minimize the patient's (replayed) exposure to hypoglycemisk risk and hyperglycemic risk are stored for future reference.

Figure 23:
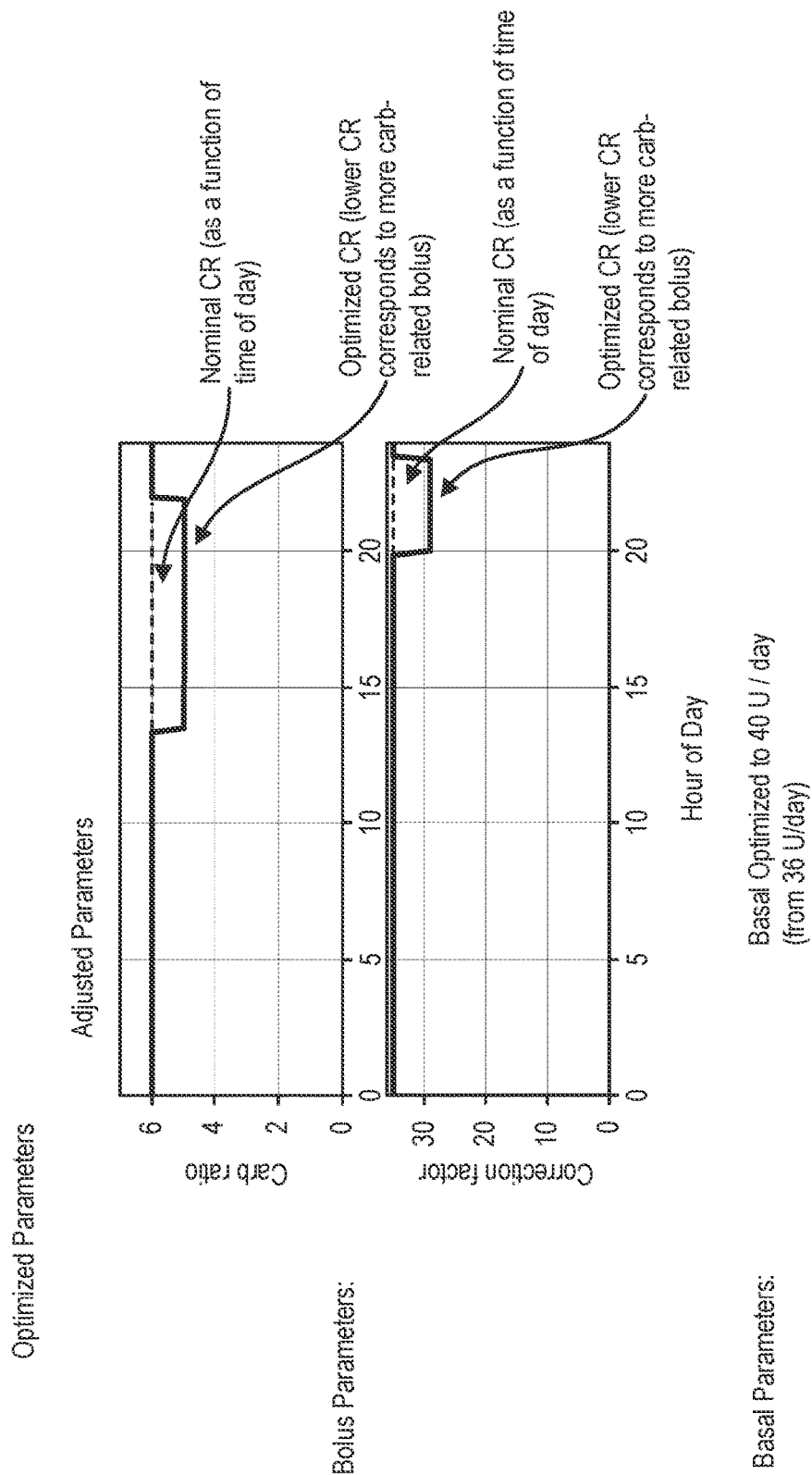
FIG. 23 is a chart showing optimized bolus and basal parameters.

After the various optimizations have run and been quantified, the best combination of parameters are selected. FIG. 23 is a chart 2300 showing optimized bolus and basal parameters.

Figure 24:
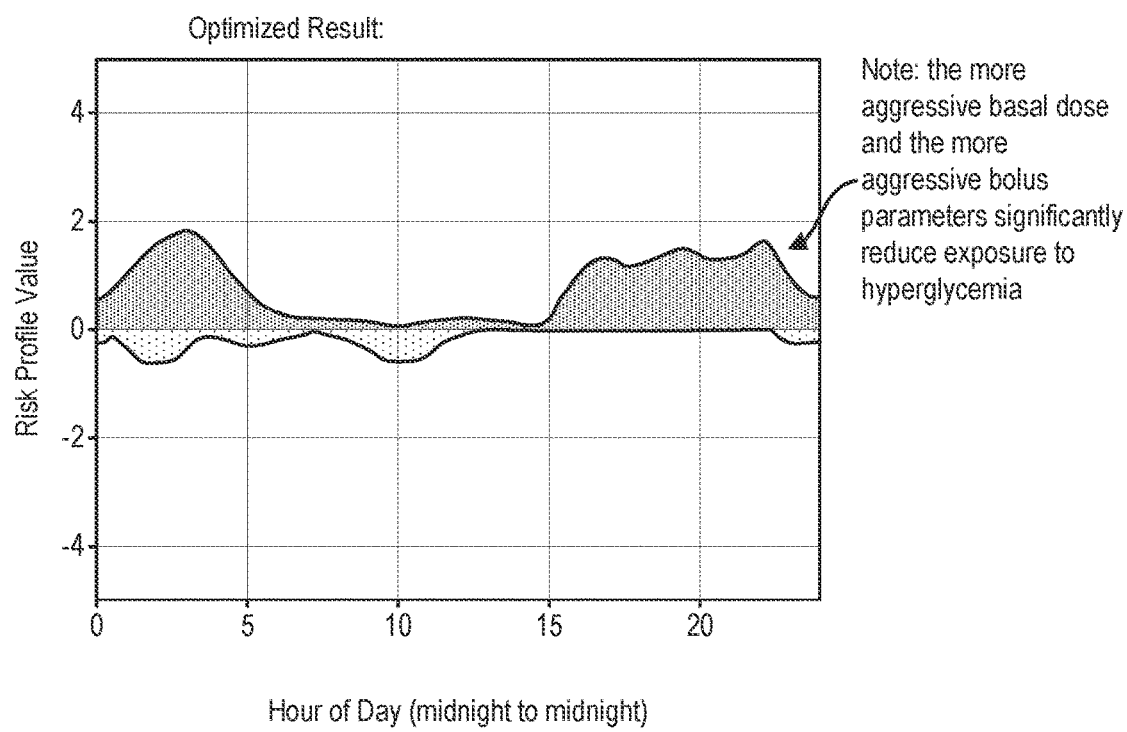
FIGS. 24 and 25 illustrate charts that show example risk profiles.
Figure 25:
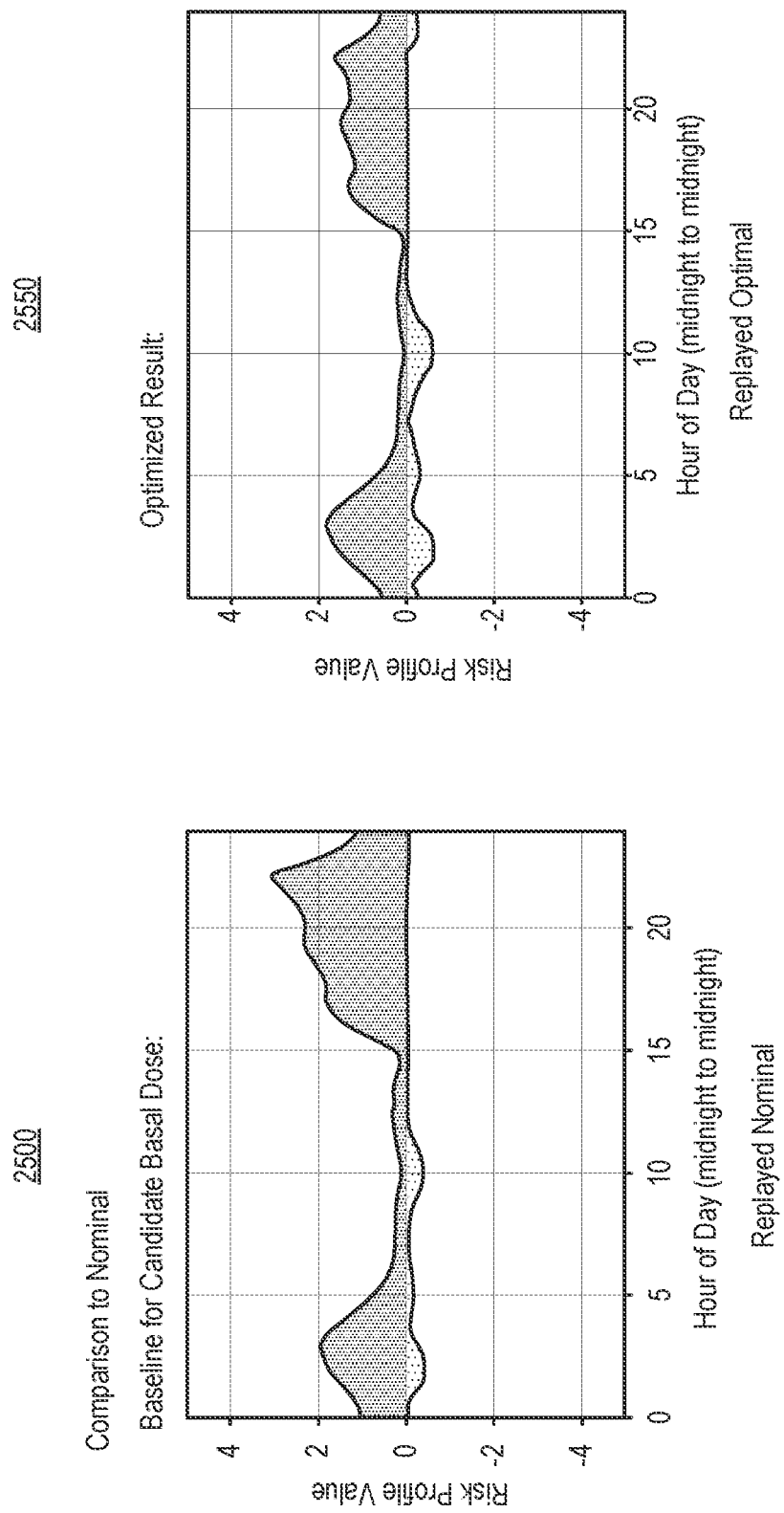

FIGS. 24 and 25 illustrate charts that show example risk profiles 2400, 2500, 2550. The risk profiles show that by applying the optimized parameters, the patient could have reduced their glycemic risk significantly, and therefore recommendations for the optimized parameters can be outputted as described in more detail herein.

In another example, wherein a patient that prefers fixed time-of-day bolusing insulin strategy, the systems and methods may receive CGM, and insulin amount and time, and identify a therapeutic opportunity as afternoon hypoglycemia for a time window (e.g., time x to time y). The insulin strategy is identified as fixed time of day bolusing based on a pattern identified in regular time of day of bolusing patterns. The insulin strategy scorer identifies a correlation with specific times of day of 85%. The insulin strategy adaptation iteratively runs percentage changes in time and amount of insulin bolusing and recommends bolusing for lunch 30 minutes sooner and/or uses 10% more insulin at normal midday bolus. The report out to patient indicates that a 30 minute shift in timing and/or 10% increase in midday fixed bolus would produce a 20% reducing in hypoglycemia, and the combination of both would produce a 25% decrease in hypoglycemia.

In yet another example, a patient that prefers mealtime bolusing without counting carbs likely uses a small, medium, large (S/M/L) meal estimation instead based on three typical bolus amounts. In this example, the data inputs include CGM, insulin amount and time, and meal time. The therapeutic opportunity is identified by a patient requesting a "bolus check-up" from the user interface. The insulin strategy identified is a mealtime bolusing strategy with three typical doses indicative of S/M/L meal estimation. The insulin strategy scorer shows a correlation with a typical carb estimator for the S/M/L estimation. The insulin strategy adaptation recommends an increase in medium boluses by 10% and/or decrease large boluses by 10%. The output reports to the patient that an increase in medium-sized boluses by 10% and a decrease of large boluses by 10% would produce an decrease in hypoglycemia and hyperglycemia, and wherein the combination of both would produce a particular percentage amount decrease (x % where x is a determined, calculated, or estimated number) in hypoglycemia and a particular percentage amount decrease (x %) in hyperglycemia.

FIG. 26 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 26, an exemplary system for implementing aspects described herein includes a computing device, such as computing device 2600. In its most basic configuration, computing device 2600 typically includes at least one processing unit 2602 and memory 2604. Depending on the exact configuration and type of computing device, memory 2604 may be volatile (such as random access memory (RAM)), non-volatile (such as read-only memory (ROM), flash memory, etc.), or some combination of the two. This most basic configuration is illustrated in FIG. 26 by dashed line 2606.

Computing device 2600 may have additional features/functionality. For example, computing device 2600 may include additional storage (removable and/or non-removable) including, but not limited to, magnetic or optical disks or tape. Such additional storage is illustrated in FIG. 26 by removable storage 2608 and non-removable storage 2610.

Computing device 2600 typically includes a variety of computer readable media. Computer readable media can be any available media that can be accessed by the device 2600 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 2604, removable storage 2608, and non-removable storage 2610 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 2600. Any such computer storage media may be part of computing device 2600.

Computing device 2600 may contain communication connection(s) 2612 that allow the device to communicate with other devices. Computing device 2600 may also have input device(s) 2614 such as a keyboard, mouse, pen, voice input device, touch input device, etc. Output device(s) 2616 such as a display, speakers, printer, etc. may also be included. All these devices are well known in the art and need not be discussed at length here.

In an implementation, a method comprises: deriving at least one single symptom-specific risk profile, using a glycemic risk profiler; determining, using a therapeutic zone assessor, at least one therapeutically correlated zone associated with the at least one single symptom-specific risk profile; determining, using a zone importance quantifier, an importance value of the at least one therapeutically correlated zone; and outputting information based on the importance value.

Implementations may include some or all of the following features. The method further comprises receiving glucose data, wherein deriving the at least one single symptom-specific risk profile uses the glucose data. The glucose data comprises at least one of CGM (continuous glucose monitoring) readings, confidence readings assigned to CGM values, self-monitoring blood glucose readings, or retrospectively calibrated or corrected CGM readings. The glucose data encompasses a time period of at least one week. The at least one single symptom-specific risk profile describes either hypoglycemic risk or hyperglycemic risk as a function of the time of day using glucose data. Deriving the at least one single symptom-specific risk profile comprises at least one of evaluating steepness (first and second order derivatives of a curve), frequency, severity, curvature, average value of profile across 24 hours, or variability of the profile (mean and standard deviation). The at least one single symptom-specific risk profile is indicative of glycemic dysfunction based the CGM signal over a selected time period, indicating recurring windows of time characterized by a predefined severity and frequency of hypoglycemia or hyperglycemia over the selected time period. The at least one single symptom-specific risk profile represents at least one of hypoglycemia isolated from hyperglycemia, or hyperglycemia isolated from hypoglycemia. Determining the at least one therapeutically correlated zone comprises identifying the at least one therapeutically correlated zone from the at least one single symptom-specific risk profile. The at least one therapeutically correlated zone is an interval of a 24 hour day in which BG data of a patient indicates that at least one of the insulin basal rate or dose or bolus strategies of the patient are systematically non-optimal. The at least one therapeutically correlated zone is identified and associated with at least one risk profile and comprises at least one interval of the day in which one or more single symptom-specific risk profiles indicate potential glycemic dysfunction.

Implementations may also include some or all of the following features. The method further comprises identifying a period of time in which the at least one single symptom-specific risk profile could be mitigated via the adjustment of parameters or timing of insulin therapy. Determining the at least one therapeutically correlated zone is based on which of least one of candidate behavioral changes or therapeutic changes are predicted to decrease a single-symptom glycemic risk without a subsequent increase in another symptom. Determining the importance value of the at least one therapeutically correlated zone comprises prioritizing the zone that is more therapeutically significant or addressable. Determining the importance value of the at least one therapeutically correlated zone comprises evaluating a magnitude of a risk. Determining the importance value of the at least one therapeutically correlated zone comprises considering at least one of the time of day or proximity of one risk profile to another risk profile. The importance value is the peak value of the at least one single symptom-specific risk profile. Deriving the at least one single symptom-specific risk profile is based on data above a particular credibility level. Outputting the information comprises outputting at least one of numerical, alphanumerical, or graphical information. Outputting the information comprises outputting at least one of behavioral changes or therapeutic changes to a therapeutic zone of time to decrease a single symptom in a time window. Outputting the information comprises outputting the information to a connected insulin pump or insulin pen, or into a bolus calculator. Outputting the information comprises outputting a graphical representation of at least one of risk profiles or therapeutically correlated zones, or relative importance of at least one of risk profiles or therapeutically correlated zones.

In an implementation, a system comprises: a glycemic risk profiler configured to derive at least one single symptom-specific risk profile; a therapeutic zone assessor configured to determine at least one therapeutically correlated zone associated with the at least one single symptom-specific risk profile; a zone importance quantifier configured to determine an importance value of the at least one therapeutically correlated zone; and a therapeutic zone report generator configured to output information based on the importance value.

Implementations may include some or all of the following features. The glycemic risk profiler is further configured to receive glucose data, wherein deriving the at least one single symptom-specific risk profile uses the glucose data. The glucose data comprises at least one of CGM (continuous glucose monitoring) readings, confidence readings assigned to CGM values, self-monitoring blood glucose readings, or retrospectively calibrated or corrected CGM readings. The glucose data encompasses a time period of at least one week. The at least one single symptom-specific risk profile describes either hypoglycemic risk or hyperglycemic risk as a function of the time of day using glucose data. Deriving the at least one single symptom-specific risk profile comprises at least one of evaluating steepness (first and second order derivatives of a curve), frequency, severity, curvature, average value of profile across 24 hours, or variability of the profile (mean and standard deviation). The at least one single symptom-specific risk profile is indicative of glycemic dysfunction based the CGM signal over a selected time period, indicating recurring windows of time characterized by a predefined severity and frequency of hypoglycemia or hyperglycemia over the selected time period. The at least one single symptom-specific risk profile represents at least one of hypoglycemia isolated from hyperglycemia, or hyperglycemia isolated from hypoglycemia. Determining the at least one therapeutically correlated zone comprises identifying the at least one therapeutically correlated zone from the at least one single symptom-specific risk profile. The at least one therapeutically correlated zone is an interval of a 24 hour day in which BG data of a patient indicates that at least one of the insulin basal rate or dose or bolus strategies of the patient are systematically non-optimal. The at least one therapeutically correlated zone is identified and associated with at least one risk profile and comprises at least one interval of the day in which one or more single symptom-specific risk profiles indicate potential glycemic dysfunction.

Implementations may also include some or all of the following features. The therapeutic zone assessor is further configured to identify a period of time in which the at least one single symptom-specific risk profile could be mitigated via the adjustment of parameters or timing of insulin therapy. Determining the at least one therapeutically correlated zone is based on which of least one of candidate behavioral changes or therapeutic changes are predicted to decrease a single-symptom glycemic risk without a subsequent increase in another symptom. Determining the importance value of the at least one therapeutically correlated zone comprises prioritizing the zone that is more therapeutically significant or addressable. Determining the importance value of the at least one therapeutically correlated zone comprises evaluating a magnitude of a risk. Determining the importance value of the at least one therapeutically correlated zone comprises considering at least one of the time of day or proximity of one risk profile to another risk profile. The importance value is the peak value of the at least one single symptom-specific risk profile. Deriving the at least one single symptom-specific risk profile is based on data above a particular credibility level. Outputting the information comprises outputting at least one of numerical, alphanumerical, or graphical information. Outputting the information comprises outputting at least one of behavioral changes or therapeutic changes to a therapeutic zone of time to decrease a single symptom in a time window. Outputting the information comprises outputting the information to a connected insulin pump or insulin pen, or into a bolus calculator. Outputting the information comprises outputting a graphical representation of at least one of risk profiles or therapeutically correlated zones, or relative importance of at least one of risk profiles or therapeutically correlated zones.

In an implementation, a system comprises: at least one processor; and a non-transitory computer readable medium comprising instructions that, when executed by the at least one processor, cause the system to: derive at least one single symptom-specific risk profile; determine at least one therapeutically correlated zone associated with the at least one single symptom-specific risk profile; determine an importance value of the at least one therapeutically correlated zone; and output information based on the importance value.

Implementations may include some or all of the following features. The system further comprises instructions that, when executed by the at least one processor, cause the system to receive glucose data, wherein deriving the at least one single symptom-specific risk profile uses the glucose data. The glucose data comprises at least one of CGM (continuous glucose monitoring) readings, confidence readings assigned to CGM values, self-monitoring blood glucose readings, or retrospectively calibrated or corrected CGM readings. The glucose data encompasses a time period of at least one week. The at least one single symptom-specific risk profile describes either hypoglycemic risk or hyperglycemic risk as a function of the time of day using glucose data. Deriving the at least one single symptom-specific risk profile comprises at least one of evaluating steepness (first and second order derivatives of a curve), frequency, severity, curvature, average value of profile across 24 hours, or variability of the profile (mean and standard deviation). The at least one single symptom-specific risk profile is indicative of glycemic dysfunction based the CGM signal over a selected time period, indicating recurring windows of time characterized by a predefined severity and frequency of hypoglycemia or hyperglycemia over the selected time period. The at least one single symptom-specific risk profile represents at least one of hypoglycemia isolated from hyperglycemia, or hyperglycemia isolated from hypoglycemia. Determining the at least one therapeutically correlated zone comprises identifying the at least one therapeutically correlated zone from the at least one single symptom-specific risk profile. The at least one therapeutically correlated zone is an interval of a 24 hour day in which BG data of a patient indicates that at least one of the insulin basal rate or dose or bolus strategies of the patient are systematically non-optimal. The at least one therapeutically correlated zone is identified and associated with at least one risk profile and comprises at least one interval of the day in which one or more single symptom-specific risk profiles indicate potential glycemic dysfunction.

Implementations may also include some or all of the following features. The system further comprises instructions that, when executed by the at least one processor, cause the system to identify a period of time in which the at least one single symptom-specific risk profile could be mitigated via the adjustment of parameters or timing of insulin therapy. Determining the at least one therapeutically correlated zone is based on which of least one of candidate behavioral changes or therapeutic changes are predicted to decrease a single-symptom glycemic risk without a subsequent increase in another symptom. Determining the importance value of the at least one therapeutically correlated zone comprises prioritizing the zone that is more therapeutically significant or addressable. Determining the importance value of the at least one therapeutically correlated zone comprises evaluating a magnitude of a risk. Determining the importance value of the at least one therapeutically correlated zone comprises considering at least one of the time of day or proximity of one risk profile to another risk profile. The importance value is the peak value of the at least one single symptom-specific risk profile. Deriving the at least one single symptom-specific risk profile is based on data above a particular credibility level. Outputting the information comprises outputting at least one of numerical, alphanumerical, or graphical information. Outputting the information comprises outputting at least one of behavioral changes or therapeutic changes to a therapeutic zone of time to decrease a single symptom in a time window. Outputting the information comprises outputting the information to a connected insulin pump or insulin pen, or into a bolus calculator. Outputting the information comprises outputting a graphical representation of at least one of risk profiles or therapeutically correlated zones, or relative importance of at least one of risk profiles or therapeutically correlated zones.

In an implementation, a method comprises: receiving glucose and insulin data; identifying a therapeutic improvement opportunity using the glucose and insulin data; determining candidate changes to insulin therapy; assessing an improvement in therapeutic risk based on the candidate changes; quantifying the improvement of the candidate changes; and outputting at least one of the candidate changes based on the improvement.

Implementations may include some or all of the following features. The glucose and insulin data is received from at least one of a patient or a connected system or device. Identifying the therapeutic improvement opportunity comprises receiving a user selection of at least one of a mealtime, a time of day, or a parameter setting. The parameter setting is a carb ratio. The candidate changes to insulin therapy comprise percentage increases or decreases to bolus therapy or basal therapy. The candidate changes to insulin therapy comprise changes to insulin delivery parameters associated with bolus therapy or basal therapy. The candidate changes are in terms of carb ratios, correction factors, basal rates, or profiles. The candidate changes comprise basal dose sensitivity. The candidate changes comprise percentage change to basal or bolus doses in therapeutic zones. Quantifying the improvement of the candidate changes comprises comparing risk profile values. Outputting at least one of the candidate changes based on the improvement comprises outputting the candidate change that provides the optimized risk profile. Outputting at least one of the candidate changes comprises providing an output in the form of a graph illustrating at least one of a candidate change or an optimized risk output to a user interface or connected device. The connected device comprises a bolus calculator. The output is provided by a natural language processor to describe a candidate change and an optimized risk outcome. The output identifies which therapeutic zones or zone groups have been optimized.

In an implementation, a system comprises: a therapeutic improvement identifier configured to evaluate collated glucose and insulin data of a patient to identify areas for therapy optimization in a diabetes management routine of the patient, and to generate a therapeutic improvement; a relative insulin optimizer configured to propose changes to a therapy, assess the impact of the changes, and quantifies an improvement associated with the changes; and a relative insulin optimizer report generator that provides an output.

Implementations may include some or all of the following features. The relative insulin optimizer comprises: a change proposer configured to propose the changes to insulin therapy; an impact assessor configured to assess the impact of candidate therapy changes by estimating the impact to a risk profile of historical glucose values; and an improvement quantifier configured to quantify an improvement of candidate therapy changes. The change proposer is further configured to propose the changes as percentage-wise changes to at least one of basal or bolus in a time window. The improvement quantifier is configured to quantify the improvement of candidate therapy changes, based on a percentage improvement or change in blood glucose outcome metrics. The relative insulin optimizer report generator is configured to output candidate therapy change to a user. The user is one of a clinician, a patient, or a connected device or system. The therapeutic improvement identifier comprises a user selection of a therapy or a time of day to be optimized. The user is a patient or a clinician. The therapeutic improvement is identified by an algorithm.

In an implementation, a system comprises: at least one processor; and a non-transitory computer readable medium comprising instructions that, when executed by the at least one processor, cause the system to: receive glucose and insulin data; identify a therapeutic improvement opportunity using the glucose and insulin data; determine candidate changes to insulin therapy; assess an improvement in therapeutic risk based on the candidate changes; quantify the improvement of the candidate changes; and output at least one of the candidate changes based on the improvement.

Implementations may include some or all of the following features. The glucose and insulin data is received from at least one of a patient or a connected system or device. Identifying the therapeutic improvement opportunity comprises receiving a user selection of at least one of a mealtime, a time of day, or a parameter setting. The parameter setting is a carb ratio. The candidate changes to insulin therapy comprise percentage increases or decreases to bolus therapy or basal therapy. The candidate changes to insulin therapy comprise changes to insulin delivery parameters associated with bolus therapy or basal therapy. The candidate changes are in terms of carb ratios, correction factors, basal rates, or profiles. The candidate changes comprise basal dose sensitivity. The candidate changes comprise percentage change to basal or bolus doses in therapeutic zones. Quantifying the improvement of the candidate changes comprises comparing risk profile values. Outputting at least one of the candidate changes based on the improvement comprises outputting the candidate change that provides the optimized risk profile. Outputting at least one of the candidate changes comprises providing an output in the form of a graph illustrating at least one of a candidate change or an optimized risk output to a user interface or connected device. The connected device comprises a bolus calculator. The output is provided by a natural language processor to describe a candidate change and an optimized risk outcome. The output identifies which therapeutic zones or zone groups have been optimized.

In an implementation, a method comprises: receiving at least one of glucose data, insulin data, or other-diabetes related data of a patient; identifying a therapeutic improvement opportunity using the at least one of glucose data, insulin data, or other-diabetes related data; identifying an insulin dosing strategy of the patient; scoring the insulin dosing strategy for patient compliance; performing optimization for the insulin dosing strategy; and providing an output comprising optimized insulin strategy parameters to a user.

Implementations may include some or all of the following features. The other diabetes-related data comprises at least one of meal information, specificity of meals, timing of meals, sizing of meals, carbohydrate estimates, composition information, or exercise information. The at least one of glucose data, insulin data, or other-diabetes related data is received from at least one of a patient or a connected system or device. Identifying the therapeutic improvement opportunity comprises receiving a user selection of at least one of a mealtime, a time of day, or a parameter setting. The parameter setting is a carb ratio. The insulin dosing strategy comprises a diabetes management or insulin strategy being implemented by the patient in practice as determined from the at least one of glucose data, insulin data, or other-diabetes related data of a patient. Performing optimization for the insulin dosing strategy determines whether the patient adheres to a known insulin strategy and analyzes the effect of percentage changes to the parameters of the identified insulin strategy. The user is at least one of a clinician, a patient, or a connected device or system. The output is provided by a natural language processor to describe a candidate change and an optimized risk outcome. Providing the output comprises providing an output in the form of a graph illustrating the optimized insulin strategy parameters to a user interface or connected device. The connected device comprises a bolus calculator.

In an implementation, a system comprises: a therapeutic improvement identifier configured to evaluate collated glucose and insulin data of a patient to identify areas for therapy optimization in a diabetes management routine of the patient, and to generate a therapeutic improvement; an insulin strategy optimizer configured to determine whether the patient adheres to a known insulin strategy and analyze the effect of percentage changes to the parameters of the identified insulin strategy; and a therapy identifier optimizer report generator that provides an output.

Implementations may include some or all of the following features. The insulin strategy optimizer comprises: an insulin strategy identifier configured to identify a diabetes management or insulin strategy being implemented by the patient in practice as determined from the collated glucose and insulin data; a compliance scorer configured to quantify a compliance of the patient with the identified insulin strategy; and an insulin strategy optimizer within identified behavior configured to perform optimization for the identified insulin strategy. The diabetes data comprises insulin data and meal data. The insulin strategy identifier is configured to identify patterns in dosing and characterizes the identified insulin strategy of the patient based thereon. The insulin strategy is the behavioral methodology that the patient applies in diabetes management, comprising at least one of types of insulin pump usage, multiple daily injections, or type 2 therapies. The compliance scorer is configured to generate a score computed for a degree of compliance of the patient with the identified insulin strategy. The insulin strategy optimizer within identified behavior is configured to iteratively propose percentage changes to the parameters of the strategy in a selected therapeutic zone or zone group. The output comprises optimized insulin strategy parameters. The therapy identifier optimizer report generator is configured to output a candidate therapy change to a user. The user is at least one of a clinician, a patient, or a connected device or system. The output is provided by a natural language processor to describe a candidate change and an optimized risk outcome.

In an implementation, a system comprises: at least one processor; and a non-transitory computer readable medium comprising instructions that, when executed by the at least one processor, cause the system to: receive at least one of glucose data, insulin data, or other-diabetes related data of a patient; identify a therapeutic improvement opportunity using the at least one of glucose data, insulin data, or other-diabetes related data; identify an insulin dosing strategy of the patient; score the insulin dosing strategy for patient compliance; perform optimization for the insulin dosing strategy; and provide an output comprising optimized insulin strategy parameters to a user.

Implementations may include some or all of the following features. The other diabetes-related data comprises at least one of meal information, specificity of meals, timing of meals, sizing of meals, carbohydrate estimates, composition information, or exercise information. The at least one of glucose data, insulin data, or other-diabetes related data is received from at least one of a patient or a connected system or device. Identifying the therapeutic improvement opportunity comprises receiving a user selection of at least one of a mealtime, a time of day, or a parameter setting. The parameter setting is a carb ratio. The insulin dosing strategy comprises a diabetes management or insulin strategy being implemented by the patient in practice as determined from the at least one of glucose data, insulin data, or other-diabetes related data of a patient. Performing optimization for the insulin dosing strategy determines whether the patient adheres to a known insulin strategy and analyzes the effect of percentage changes to the parameters of the identified insulin strategy. The user is at least one of a clinician, a patient, or a connected device or system. The output is provided by a natural language processor to describe a candidate change and an optimized risk outcome. Providing the output comprises providing an output in the form of a graph illustrating the optimized insulin strategy parameters to a user interface or connected device. The connected device comprises a bolus calculator.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for reducing glycemic dysfunction, comprising:
    deriving at least one single symptom-specific risk profile, using a glycemic risk profiler;
    determining, using a therapeutic zone assessor, at least one therapeutically correlated zone associated with the at least one single symptom-specific risk profile, the at least one therapeutically correlated zone being a window of time during which an insulin therapy is non-optimal such that insulin therapy adjustments are able to be made that provide systematic improvements of glycemic outcomes;
    determining, using a zone importance quantifier, an importance value of the at least one therapeutically correlated zone; and
    outputting information based on the importance value to cause an adjustment to insulin therapy delivered by an insulin delivery device.

2. The method of claim 1, further comprising receiving glucose data, wherein deriving the at least one single symptom-specific risk profile uses the glucose data, wherein the glucose data comprises at least one of CGM (continuous glucose monitoring) readings, confidence readings assigned to CGM values, self-monitoring blood glucose readings, or retrospectively calibrated or corrected CGM readings.

3. The method of claim 2, wherein the glucose data encompasses a time period of at least one week.

4. The method of claim 1, wherein deriving the at least one single symptom-specific risk profile comprises at least one of evaluating steepness (first and second order derivatives of a curve), frequency, severity, curvature, average value of profile across 24 hours, or variability of the profile (mean and standard deviation).

5. The method of claim 1, wherein the at least one single symptom-specific risk profile: describes either hypoglycemic risk or hyperglycemic risk as a function of the time of day using glucose data; or is indicative of glycemic dysfunction based the CGM signal over a selected time period, indicating recurring windows of time characterized by a predefined severity and frequency of hypoglycemia or hyperglycemia over the selected time period; or represents at least one of hypoglycemia isolated from hyperglycemia, or hyperglycemia isolated from hypoglycemia.

6. The method of claim 1, wherein determining the at least one therapeutically correlated zone comprises identifying the at least one therapeutically correlated zone from the at least one single symptom-specific risk profile.

7. The method of claim 1, wherein the at least one therapeutically correlated zone is an interval of a 24 hour day in which BG data of a patient indicates that at least one of the insulin basal rate or dose or bolus strategies of the patient are systematically non-optimal.

8. The method of claim 1, wherein the at least one therapeutically correlated zone is identified and associated with at least one risk profile and comprises at least one interval of the day in which one or more single symptom-specific risk profiles indicate potential glycemic dysfunction.

9. The method of claim 1, further comprising identifying a period of time in which the at least one single symptom-specific risk profile could be mitigated via the adjustment of parameters or timing of insulin therapy.

10. The method of claim 1, wherein determining the at least one therapeutically correlated zone is based on which of least one of candidate behavioral changes or therapeutic changes are predicted to decrease a single-symptom glycemic risk without a subsequent increase in another symptom.

11. The method of claim 1, wherein determining the importance value of the at least one therapeutically correlated zone comprises: prioritizing the zone that is more therapeutically significant or addressable; or evaluating a magnitude of a risk; or considering at least one of the time of day or proximity of one risk profile to another risk profile.

12. The method of claim 1, wherein the importance value is the peak value of the at least one single symptom-specific risk profile.

13. The method of claim 1, wherein deriving the at least one single symptom-specific risk profile is based on data above a particular credibility level.

14. The method of claim 1, wherein outputting the information comprises: outputting at least one of numerical, alphanumerical, or graphical information; or outputting at least one of behavioral changes or therapeutic changes to a therapeutic zone of time to decrease a single symptom in a time window; or outputting the information to a connected insulin pump or insulin pen, or into a bolus calculator; or outputting a graphical representation of at least one of risk profiles or therapeutically correlated zones, or relative importance of at least one of risk profiles or therapeutically correlated zones.

15. A system for reducing glycemic dysfunction comprising:
  a glycemic risk profiler configured to derive at least one single symptom-specific risk profile;
  a therapeutic zone assessor configured to determine at least one therapeutically correlated zone associated with the at least one single symptom-specific risk profile, the at least one therapeutically correlated zone being a window of time during which an insulin therapy is non-optimal such that insulin therapy adjustments are able to be made that provide systematic improvements of glycemic outcomes;
  a zone importance quantifier configured to determine an importance value of the at least one therapeutically correlated zone; and
  a therapeutic zone report generator configured to output information based on the importance value to cause an adjustment to insulin therapy delivered by an insulin delivery device.

16. The system of claim 15, wherein the glycemic risk profiler is further configured to receive glucose data, wherein deriving the at least one single symptom-specific risk profile uses the glucose data, wherein the glucose data comprises at least one of CGM (continuous glucose monitoring) readings, confidence readings assigned to CGM values, self-monitoring blood glucose readings, or retrospectively calibrated or corrected CGM readings.

17. The system of claim 16, wherein the glucose data encompasses a time period of at least one week.

18. The system of claim 15, wherein the at least one single symptom-specific risk profile describes either hypoglycemic risk or hyperglycemic risk as a function of the time of day using glucose data.

19. The system of claim 15, wherein deriving the at least one single symptom-specific risk profile comprises at least one of evaluating steepness (first and second order derivatives of a curve), frequency, severity, curvature, average value of profile across 24 hours, or variability of the profile (mean and standard deviation).

20. The system of claim 15, wherein the at least one single symptom-specific risk profile is indicative of glycemic dysfunction based the CGM signal over a selected time period, indicating recurring windows of time characterized by a predefined severity and frequency of hypoglycemia or hyperglycemia over the selected time period.

21. The system of claim 15, wherein the at least one single symptom-specific risk profile represents at least one of hypoglycemia isolated from hyperglycemia, or hyperglycemia isolated from hypoglycemia.

22. The system of claim 15, wherein determining the at least one therapeutically correlated zone comprises identifying the at least one therapeutically correlated zone from the at least one single symptom-specific risk profile.

23. The system of claim 15, wherein the at least one therapeutically correlated zone is an interval of a 24 hour day in which BG data of a patient indicates that at least one of the insulin basal rate or dose or bolus strategies of the patient are systematically non-optimal.

24. The system of claim 15, wherein the at least one therapeutically correlated zone is identified and associated with at least one risk profile and comprises at least one interval of the day in which one or more single symptom-specific risk profiles indicate potential glycemic dysfunction.

25. The system of claim 15, wherein the therapeutic zone assessor is further configured to identify a period of time in which the at least one single symptom-specific risk profile could be mitigated via the adjustment of parameters or timing of insulin therapy.

26. The system of claim 15, wherein determining the at least one therapeutically correlated zone is based on which of least one of candidate behavioral changes or therapeutic changes are predicted to decrease a single-symptom glycemic risk without a subsequent increase in another symptom.

27. The system of claim 15, wherein determining the importance value of the at least one therapeutically correlated zone comprises: prioritizing the zone that is more therapeutically significant or addressable; or evaluating a magnitude of a risk; or considering at least one of the time of day or proximity of one risk profile to another risk profile.

28. The system of claim 15, wherein the importance value is the peak value of the at least one single symptom-specific risk profile.

29. The system of claim 15, wherein deriving the at least one single symptom-specific risk profile is based on data above a particular credibility level.

30. The system of claim 15, wherein outputting the information comprises: outputting at least one of numerical, alphanumerical, or graphical information; or outputting at least one of behavioral changes or therapeutic changes to a therapeutic zone of time to decrease a single symptom in a time window; or outputting the information to a connected insulin pump or insulin pen, or into a bolus calculator; or outputting a graphical representation of at least one of risk profiles or therapeutically correlated zones, or relative importance of at least one of risk profiles or therapeutically correlated zones.

31. A system for reducing glycemic dysfunction comprising:
  at least one processor; and
  a non-transitory computer readable medium comprising instructions that, when executed by the at least one processor, cause the system to:
    derive at least one single symptom-specific risk profile;
    determine at least one therapeutically correlated zone associated with the at least one single symptom-specific risk profile, the at least one therapeutically correlated zone being a window of time during which an insulin therapy is non-optimal such that insulin therapy adjustments are able to be made that provide systematic improvements of glycemic outcomes;
    determine an importance value of the at least one therapeutically correlated zone; and output information based on the importance value to cause an adjustment to insulin therapy delivered by an insulin delivery device.

32. The system of claim 31, further comprising instructions that, when executed by the at least one processor, cause the system to receive glucose data, wherein deriving the at least one single symptom-specific risk profile uses the glucose data, wherein the glucose data comprises at least one of CGM (continuous glucose monitoring) readings, confidence readings assigned to CGM values, self-monitoring blood glucose readings, or retrospectively calibrated or corrected CGM readings.

33. The system of claim 32, wherein the glucose data encompasses a time period of at least one week.

34. The system of claim 31, wherein the at least one single symptom-specific risk profile describes either hypoglycemic risk or hyperglycemic risk as a function of the time of day using glucose data.

35. The system of claim 31, wherein deriving the at least one single symptom-specific risk profile comprises at least one of evaluating steepness (first and second order derivatives of a curve), frequency, severity, curvature, average value of profile across 24 hours, or variability of the profile (mean and standard deviation).

36. The system of claim 31, wherein the at least one single symptom-specific risk profile: is indicative of glycemic dysfunction based the CGM signal over a selected time period, indicating recurring windows of time characterized by a predefined severity and frequency of hypoglycemia or hyperglycemia over the selected time period; or represents at least one of hypoglycemia isolated from hyperglycemia, or hyperglycemia isolated from hypoglycemia.

37. The system of claim 31, wherein determining the at least one therapeutically correlated zone comprises identifying the at least one therapeutically correlated zone from the at least one single symptom-specific risk profile.

38. The system of claim 31, wherein the at least one therapeutically correlated zone is an interval of a 24 hour day in which BG data of a patient indicates that at least one of the insulin basal rate or dose or bolus strategies of the patient are systematically non-optimal.

39. The system of claim 31, wherein the at least one therapeutically correlated zone is identified and associated with at least one risk profile and comprises at least one interval of the day in which one or more single symptom-specific risk profiles indicate potential glycemic dysfunction.

40. The system of claim 31, further comprising instructions that, when executed by the at least one processor, cause the system to identify a period of time in which the at least one single symptom-specific risk profile could be mitigated via the adjustment of parameters or timing of insulin therapy.

41. The system of claim 31, wherein determining the at least one therapeutically correlated zone is based on which of least one of candidate behavioral changes or therapeutic changes are predicted to decrease a single-symptom glycemic risk without a subsequent increase in another symptom.

42. The system of claim 31, wherein determining the importance value of the at least one therapeutically correlated zone comprises: prioritizing the zone that is more therapeutically significant or addressable; or evaluating a magnitude of a risk; or considering at least one of the time of day or proximity of one risk profile to another risk profile.

43. The system of claim 31, wherein the importance value is the peak value of the at least one single symptom-specific risk profile.

44. The system of claim 31, wherein deriving the at least one single symptom-specific risk profile is based on data above a particular credibility level.

45. The system of claim 31, wherein outputting the information comprises: outputting at least one of numerical, alphanumerical, or graphical information; or outputting at least one of behavioral changes or therapeutic changes to a therapeutic zone of time to decrease a single symptom in a time window; or outputting the information to a connected insulin pump or insulin pen, or into a bolus calculator; or outputting a graphical representation of at least one of risk profiles or therapeutically correlated zones, or relative importance of at least one of risk profiles or therapeutically correlated zones.

* * * * *